United States Patent van der Geer et al.

[11] Patent Number: 6,028,053
[45] Date of Patent: Feb. 22, 2000

[54] PEPTIDE INHIBITORS OF A PHOSPHOTYROSINE-BINDING DOMAIN CONTAINING PROTEIN

[75] Inventors: Peter van der Geer; Sandra Wiley, both of Solana Beach, Calif.; Gerald Gish, Dona Mills; Anthony Pawson, Toronto, both of Canada; Kazunori Toma, Sagamihara, Japan

[73] Assignees: Mount Sinai Hospital Corporation, Toronto, Canada; Asahi Chemical Industry Co., Ltd., Tokyo, Japan

[21] Appl. No.: 09/051,934

[22] PCT Filed: Oct. 24, 1996

[86] PCT No.: PCT/US96/17080

§ 371 Date: Apr. 22, 1998

§ 102(e) Date: Apr. 22, 1998

[87] PCT Pub. No.: WO97/15318

PCT Pub. Date: May 1, 1997

Related U.S. Application Data

[60] Provisional application No. 60/005,944, Oct. 27, 1995, provisional application No. 60/010,384, Jan. 22, 1996, and provisional application No. 60/011,799, Feb. 20, 1996.

[51] Int. Cl.[7] .......................... A61K 38/08; A61K 38/10; A61K 38/12; C07K 7/06; C07K 7/08
[52] U.S. Cl. ..................... 514/7; 530/321; 530/326; 530/327; 530/328; 530/329; 530/345
[58] Field of Search .................... 514/7; 530/317, 530/321, 326, 327, 328, 329, 345

[56] References Cited

U.S. PATENT DOCUMENTS

| | | | |
|---|---|---|---|
| 5,352,660 | 10/1994 | Pawson | 514/12 |
| 5,434,064 | 7/1995 | Schlessinger et al. | 435/172.3 |
| 5,463,023 | 10/1995 | Schreiber et al. | 530/327 |
| 5,580,979 | 12/1996 | Bachovchin | 540/509 |

FOREIGN PATENT DOCUMENTS

| | | |
|---|---|---|
| 95/18823 | 7/1995 | WIPO . |
| 96/11664 | 4/1996 | WIPO . |
| WO96/32411 | 10/1996 | WIPO . |

OTHER PUBLICATIONS

Laminet et al., Affinity, Specificity, and Kinetics . . . J. Biol. Chem. vol. 271, No. 1, pp. 264–269, Jan. 5, 1996.
Zhou et al. Structure and ligand recognition . . . Nature, vol. 378, pp. 584–592, Dec. 7, 1995.
Trub et al. Specificity of the PTB domain of Shc . . . J. Biol. Chem. vol. 270, No. 31, pp. 18205–18208, Aug. 4, 1995.
Obermeier et al. Identification of Trk Binding Sites . . . J. Biol. Chem. vol. 268, No. 31, pp. 22963–22966, Nov. 5, 1993.
Herresa et al. An antipeptide antibody that specifically . . . PNAS, vol. 82, pp. 7899–7903, Dec. 1985.
Lemmon et al. Thermodynamic Studies of Tyrosyl . . . Biochemistry, vol. 33, pp. 5070–5076, 1994.
Shoelson et al. Distinct Mechanisms for Phosphopeptide . . . Peptides: Chemistry, Structure and Biology, 14th Symp. pp. 391–393, 1996.

(List continued on next page.)

*Primary Examiner*—Jeffrey E. Russel
*Attorney, Agent, or Firm*—Howson and Howson

[57] ABSTRACT

A peptide of the formula (I): $X^1$-$A^1$-$A^2$-$X^2$-Asn-$X^3$-$X^4$-P.Tyr-$X^5$-$X^6$-$X^7$-$X^8$, wherein $X^1$ represents Lys, Arg, His, Ser, Thr, Tyr, Asn, Leu, Val or Glu, $A^1$ represents Trp, Leu, Ala, Ser, Ile, Glu, Met, Gly, Cys, Phe, Pro or Val, and $A^2$ represents Ala, Val, Leu, Ile, Ser, Met, Phe, Gly, Cys, Trp or Pro, $X^2$ represents Glu, Asn, Tyr, Thr, Ser, Asp or Ile, $X^3$ represents Pro, Met, Trp, Phe, Ala, Lys, Val, Leu, Ile, Gly or Ser, $X^6$ represents Ser, Thr, Tyr, Asn, Glu, Met, Ala, Leu, Val or Gly, $X^7$ represents Asp, Glu, Ala, Val, Leu, Ile, Gly, Cys, Phe, Trp, Met, Pro, Ser or Asn and $X^8$ which may be present or absent represents Phe, Trp, Pro, Leu, Ala, Val, Ile, Gly, Cys, Met, Asp, Ser or Arg which interferes with the interaction of a PTB domain containing protein with a PTB domain binding site, and truncations and analogues of the peptide.

26 Claims, 20 Drawing Sheets

OTHER PUBLICATIONS

Van der Geer et al. A conserved amino–terminal Shc . . . Current Biology, vol. 5, No. 4, pp. 404–412, 1995.

J.M. Backer, C.R. Kahn, D.A. Cahill, A. Ullrich and M.F. White (1990) J. Biol. Chem., 265, 16450–26454.

A.G. Batzer, D. Rotin, J.M. Urena, E.Y. Skolnik and J. Schlessinger (1994) Mol. Cell. Biol., 14,5192–5201.

P. Blaikie, D. Immanuel, J. Wu, N. Li, V. Yainik and B. Margolis (1994) J. Biol. Chem., 269, 32031–32034.

L. Buday and J. Downward (1993) Cell, 73, 611–620.

L.A. Burns, L.M. Karnitz, S.L. Sutor and R.T. Abraham (1993) J. Biol. Chem., 268, 17659–17661.

K.S. Campbell, E. Orgis, B. Burke, W. Su, K.R. Auger, B.J. Druker, B.S. Schaffhausen, T.M. Robert and D.C. Pallas (1994) Proc. Nat. Acad. Sci. USA, 91, 6344–6348.

A.J. Crowe, J. McGlade, T. Pawson and M.J. Hayman (1994) Oncogene,9, 537–544.

R.L. Cutler, L. Liu, J.E. Damen and G. Krystal (1993) J. Biol. Chem., 268, 21463–21465.

S.M. Dilworth, C.E. Brewster, M.D. Jones, L. Lanfrancone, G. Pelicci and P.G. Pelicci (1994) Nature, 367, 87–90.

S.E. Egan, B.W. Giddings, M.W. Brooks, L. Buday, A.M. Sizeland and R.A. Weinberg (1993) Nature, 363, 45–51.

J.R. Forsayeth, A. Montemurro, B.A. Maddux, R. DePirro and I.D. Goldfine (1987) J. Biol. Chem., 262, 4134–4140.

N.W. Gale, S. Kaplan, E.J. Lowenstein, J. Schlessinger and D. Bar–Sagi (1993) Nature, 363, 88–92.

T.A. Gustafson, W. He, A. Craparo, C.D. Schaub and T.J. O'Neill (1995) Mol. Cell. Biol., 15, 2500–2508.

B.L. Hempstead, S.J. Rabin, L. Kaplan, S. Reid, L. Parada and D.R. Kaplan (1992) Neuron,9, 883–896.

A.M. Honegger, T.J. Dull, S. Felder, E. Van Obberghen, F. Bellot, d. Szapary, A. schmidt, A. Ullrich and J. schlessinger (1987) Cell, 51, 199–209.

W.M. Kavanaugh, C.W. Turck and L.T. Williams (1995) Science, 268, 1177–1179.

W.M. Kavanaugh and L.T. Williams (1994) Science, 266, 1862–1865.

K.S. Kovacina and R.A. Roth (1993) Biochem. Biophys. Res. Commun., 192, 1303–1311.

K.M. V. Lai, J.P. Olivier, G.D. Gish, M. Henkemeyer, J. McGlade and T. Pawson (1995) Mol. Cell. Biol., 15: 4810–4818.

L. Lanfrancone, G. Pelicci, M.F. Brizzi, M.G. Arouica, C. Casciari, S. Giuli, L. Pegararo, T. Pawson and P.G. Pelicci (1995) Oncogene, 10, 905–917.

N. Li, A. Batzer, R. Daly, V. Yajnik, E. Skolnik, P. Chardin, D. Bar–Sagi, B. Margolis and J. Schlessinger (1993) Nature, 363, 85–88.

L.E.M. Marengere and T. Pawson (1992) J. Biol. Chem., 267, 22779–22786.

B.J. Mayer, P.K. Jackson, R.A. Van Etten and D. Baltimore (1992) Mol. Cell. Biol., 12, 609–618.

M.J. Myer, L.M. Wang, X.J. Sun, Y. Zhang, L. Yenush, J. Schlessinger, J.H. Pierce and M.F. White (1994) Mol. Cell. Biol., 14, 3577–3587.

A. Obermeier, R.A. Bradshaw, K. Seedorf, A. Choidas, J. Schlessinger and A. Ullrich (1994) EMBO J., 13, 1585–1590.

Y. Okabayashi, Y. Kido, T. Okutani, Y. Sugimoto, K. Sakaguchi and M. Kasuga (1994) J. Biol. Chem., 269, 18674–18678.

T. Pawson (1995) Nature, 373, 573–580.

T. Pawson and G.D. Gish (1992) Cell, 71, 359–362.

G. Pelicci, L. Lanfrancone, F. Grignani, J. McGlade, F. Cavallo, G. Formi, I. Nicoletti, F. Grignani, T. Pawson and P.G. Pelicci (1992) Cell, 70,93–104.

G.J. Pronk, J. McGlade, G. Pelicci, T. Pawson and J.L. Bos (1993) J. Biol. Chem., 268, 5748–5753.

L. Puil, J. Liu, G.D. Gish, G. Mbamalu, D. Bowtell, P.G. Pelicci, R. Arlinghaus and T. Pawson (1994) EMBO J., 13, 764–773.

K.S. Ravichandran, K.K. Lee, Z. Songyang, L.C. Cantley, P. Burn and S.J. Burakoff (1993) S cience, 262,902–905.

R.A. Roth, D.J. Cassell, K.Y. Wong, B.A. Maddux and I.D. Goldfine (1982) Proc. Natl. Acad. Sci. USA, 79, 7312–7316.

M. Rozakis–Adcock, R. Fernley, J. Wade, T. Pawson and D. Bowtell (1993) Nature, 363, 83–85.

P.G. Pelicci, J. Schlessinger and T. Pawson (1992) Nature, 360, 689–692.

A.E. Salcini, J. McGlade, G. Pelicci, I. Nicoletti, T. Pawson and P.G. Pelicci (1994) Oncogene, 9, 2827–2836.

T. Sasaoka, B. Draznin, J.W. Leitner, W.J. Langlois and J.M. Olefsky (1994) J. Biol. Chem., 269, 10734–10738.

O. Segatto, G. Pelicci, S. Giuli, G. Digiesi, F.P. Di, J. McGlade, T. Pawson and P.G. Pelicci (1993) Oncogene, 8, 2105–2112.

Z. Songyang, B. Margolis, M. Chaudhuri, S.E. Shoelson and L.C. Cantley (1995) J. Biol. Chem., 270, 14863–14866.

Z. Songyang, S.E. Shoelson, J. McGlade, P. Olivier, T. Pawson, X.R. Bustelo, M. Barbacid, H. Sabe, H. Hanafusa, T. Yi, R. Ren, D. Baltimore, S. Ratnofsky, R.A. Feldman and L.C. Cantley (1994) Mol. Cell. Biol., 14, 2777–2785.

H. Hanafusa, T. Yi, R. Ren, d. Baltimore, S. Ratnofsky, R.A. Feldman and L.C. Cantley (1994) Mol. Cell. Biol., 14, 2777–2785.

R.M. Stephens, D.M. Loeb, T.D. Copeland, T. Pawson, L.A. Greene and D.R. Kaplan (1994) Neuron, 12, 691–705.

P. van der Geer and T. Pawson (1995) TIBS, 20, 277–280.

M.F. White, J.N. Livingston, J.M. Backer, V. Lauris, T.J. Dull, A. Ullrich and C.R. Kahn (1988) Cell, 54, 641–649.

K. Yokote, s. Mori, K. Hansen, J. McGlade, T. Pawson, C.H. Heldin and W.L. Claesson (1994) J. Biol. Chem., 269, 15337–15343.

K. Yonezawa, A. Ando, Y. Kaburagi, R. Yamamoto–Honda, T. Kitamura, K. Hara, M. Nakafuku, Y. Okabayashi, T. Kadowaki, Y. Kaziro and M. Kazuga (1994) J. Biol. Chem., 269, 4634–4640.

Damen, J.E. et al., Blood 82(8): 2296–2303 (1993).

Ulysse, L., Cubillos, J. and Chmielewski, J., Photoregulation of Cycle Peptide Conformation, J.A. Chem. Soc., vol. 117, No. 32, 1995, pp. 8466–8467.

Bork, P. and Margolis, B., A Phosphotyrosine Interaction Domain, Cell, vol. 80, 1995, pp. 693–694.

Raptis, L.H. et al., Electroporation of Peptides into Adherent Cells In Situ, BioTechniques, vol. 18, No. 1, 1995, pp. 104–114.

Raptis, L. and Firth, K., Laboratory Methods Electroporation of Adherent Cells In Situ, DNA and Cell Biology, vol. 9, No. 8, 1990, pp. 615–621.

FIGURE 7

```
                    p52
                     ↓
Shc   MNKLSGGGGRRTRVEGGQLGGEEWTRHGSFVNKPTRGWLHIPNDKVMGPGVSYIVRYMGCVEVLQSMRALDENTRTQVTREATSLVCEAVPGAKGATRRRKPCSRP  105
mShc  MNKLSGGGGRRTRVEGGQLGGEEWTRHGSFVNKPTRGWLHIPNDKVMGPGVSYIVRYMGCVEVLQSMRALDENTRTQVTREATSLVCEAVPGAKGATRRRKPCSRP  105
dShc  MPKNGDAGGR----------SGSGTISDGC----------IYDDVIMGVGVAFNVRYIGCVEVKTSMKSLDFFTRTQLARECINRVCEA-AGLKSAGKRLT----  82 p46
                                                     ↓
Shc   LSSILGRSNLKFAGMPITLTVSPSSLNLMAADCKQIIANHIMQSISFASGGDPDTAEYVAVVAKDPVNQRACHIILECPEGLAQDVISTIGQAFELRFKQYLRNPP  210
mShc  LSSILGRSNLKFAGMPITLTVSPSSLNLMAADCKQIIANHIMQSISFASGGDPDTAEYVAVVAKDPVNQRACHIILECPEGLAQDVISTIGQAFELRFKQYLRNPP  210
dShc  -NFISDRPSMQHAGTNIIINVSSRAESISNVETGEVIANHMPRISFASGGDNDTLDFIAVIAKNEDEWRACYVLECAGGQSEDLIVTIGKAFALRFNALSR----  183

Shc   KLVTPIHDRMAGFDGSAWDEEEEPPDIIQYYNDFPGKEPPLGGVVDMRLREGAAPGAARPTAPNEQTPSIILGATIPVGQPVGGDPEVRKQMPPPPPCP  307
mShc  KLVTPIHDRMAGFDGSAWDEEEEPPDIIQYYNDFPGKEPPLGGVVDMRLREGAA----RPTLPSAQMSSIILGATLPIGQHAAGDIIEVRKQMFLPPPCP  303
dShc  --LNDPSADCNINQSCKENVKE------YYNDLPNKIPP------EVPEPQQQQVQQLIIEPRVAQLNLKKPRDRLSSNLID----LNSPPP--       259
```

FIGURE 14
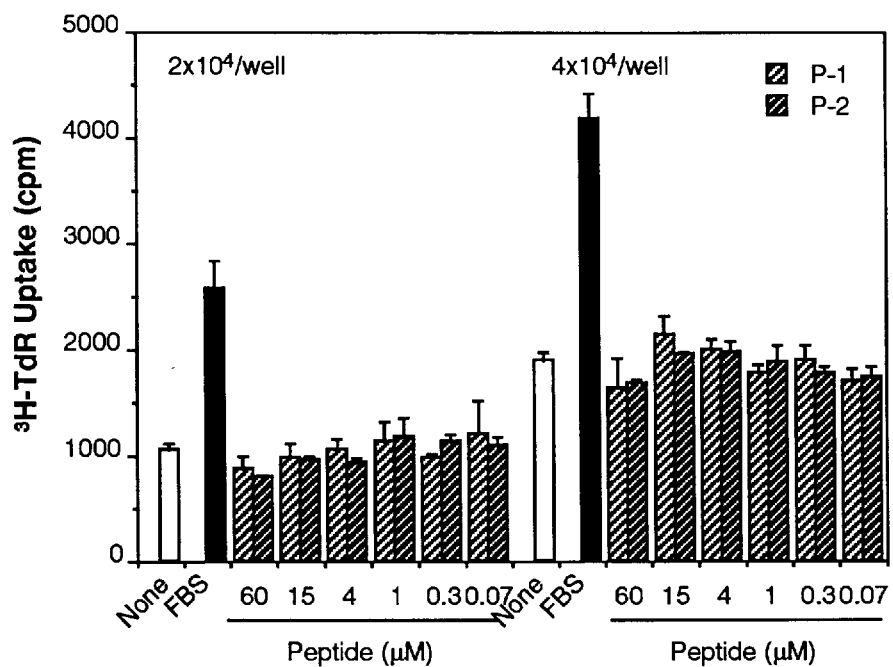
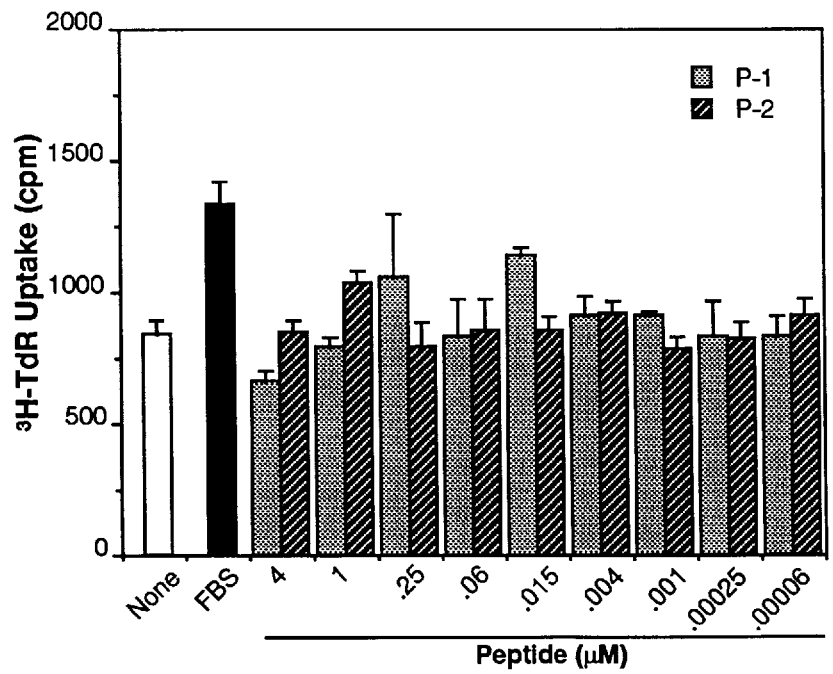

FIGURE 16
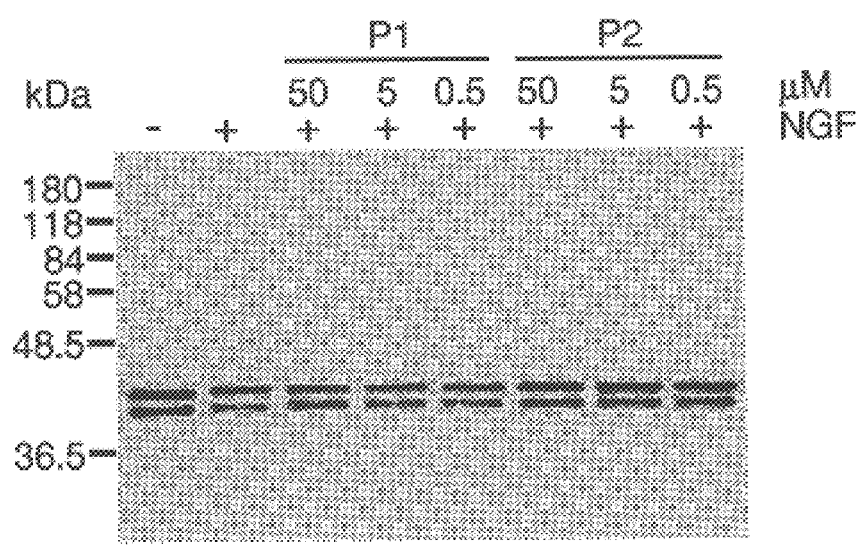
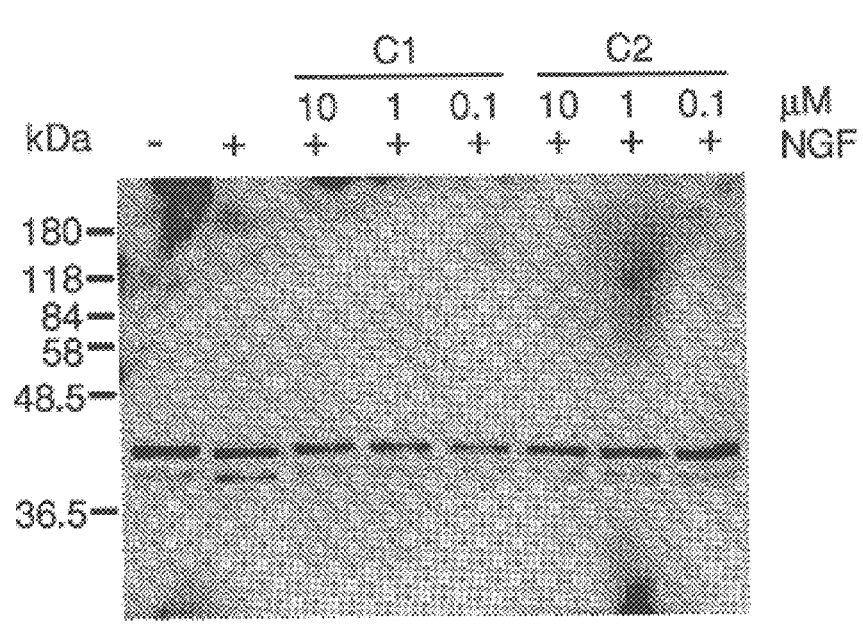

SEQUENCE LISTING

```
<160> NUMBER OF SEQ ID NOS: 60

<210> SEQ ID NO 1
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 1

His Ile Ile Glu Asn Pro Gln Tyr Phe Ser Asp
  1               5                  10

<210> SEQ ID NO 2
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 2

His Ala Ile Glu Asn Pro Gln Tyr Phe Ser Asp
  1               5                  10

<210> SEQ ID NO 3
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 3

His Ile Ala Glu Asn Pro Gln Tyr Phe Ser Asp
  1               5                  10

<210> SEQ ID NO 4
<211> LENGTH: 11
<212> TYPE: PRT
<213> ORGANISM: phosphotyrosine binding domain
<220> FEATURE:
<221> NAME/KEY: MOD_RES
<222> LOCATION: (7)
<223> OTHER INFORMATION: Phosphorylated at Tyr

<400> SEQUENCE: 4
```

```
Ile Ile Glu Asn Pro Gln Tyr Phe Ser Asp Ala
 1               5                  10

<210> SEQ ID NO 5
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr in position number 8

<400> SEQUENCE: 5

Tyr Ala Ile Ser Asn Pro Glu Tyr Leu Ser Ala
 1               5                  10

<210> SEQ ID NO 6
<211> LENGTH: 12
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 6

Thr Trp Ile Glu Asn Lys Leu Tyr Gly Met Ser Asp
 1               5                  10

<210> SEQ ID NO 7
<211> LENGTH: 12
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 7

Thr Trp Ile Glu Asn Lys Leu Tyr Gly Thr Ser Asp
 1               5                  10

<210> SEQ ID NO 8
<211> LENGTH: 12
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 8

Leu Leu Leu Ser Asn Pro Ala Tyr Arg Leu Leu Leu
 1               5                  10

<210> SEQ ID NO 9
<211> LENGTH: 12
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr in position number 8

<400> SEQUENCE: 9

Tyr Ala Ser Ser Asn Pro Glu Tyr Leu Ser Ala Ser
 1               5                  10
```

-continued

```
<210> SEQ ID NO 10
<211> LENGTH: 12
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 10

Val Ser Val Asp Asn Pro Glu Tyr Leu Leu Asn Ala
 1               5                  10

<210> SEQ ID NO 11
<211> LENGTH: 12
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 11

Ser Leu Leu Ser Asn Pro Thr Tyr Ser Val Met Arg
 1               5                  10

<210> SEQ ID NO 12
<211> LENGTH: 12
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 12

Asn Glu Met Ile Asn Pro Asn Tyr Ile Gly Met Gly
 1               5                  10

<210> SEQ ID NO 13
<211> LENGTH: 12
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 13

Glu Met Phe Glu Asn Pro Leu Tyr Gly Ser Val Ser
 1               5                  10

<210> SEQ ID NO 14
<211> LENGTH: 7
<212> TYPE: PRT
<213> ORGANISM: phosphotyrosine binding domain
<220> FEATURE:
<221> NAME/KEY: MOD_RES
<222> LOCATION: (6)
<223> OTHER INFORMATION: Phosphorylated at Tyr

<400> SEQUENCE: 14

Ile Glu Asn Pro Gln Tyr Phe
 1               5

<210> SEQ ID NO 15
<211> LENGTH: 8
<212> TYPE: PRT
```

```
<213> ORGANISM: phosphotyrosine binding domain
<220> FEATURE:
<221> NAME/KEY: MOD_RES
<222> LOCATION: (6)
<223> OTHER INFORMATION: Phosphorylated at Tyr

<400> SEQUENCE: 15

Ile Glu Asn Pro Gln Tyr Phe Ser
 1               5

<210> SEQ ID NO 16
<211> LENGTH: 7
<212> TYPE: PRT
<213> ORGANISM: phosphotyrosine binding domain
<220> FEATURE:
<221> NAME/KEY: MOD_RES
<222> LOCATION: (6)
<223> OTHER INFORMATION: Phosphorylated at Tyr

<400> SEQUENCE: 16

Ala Glu Asn Pro Gln Tyr Phe
 1               5

<210> SEQ ID NO 17
<211> LENGTH: 10
<212> TYPE: PRT
<213> ORGANISM: phosphotyrosine binding domain
<220> FEATURE:
<221> NAME/KEY: MOD_RES
<222> LOCATION: (6)
<223> OTHER INFORMATION: Phosphorylated at Tyr

<400> SEQUENCE: 17

Ile Glu Asn Pro Gln Tyr Phe Ser Pro Gly
 1               5                  10

<210> SEQ ID NO 18
<211> LENGTH: 7
<212> TYPE: PRT
<213> ORGANISM: phosphotyrosine binding domain
<220> FEATURE:
<221> NAME/KEY: MOD_RES
<222> LOCATION: (6)
<223> OTHER INFORMATION: Phosphorylated at Tyr

<400> SEQUENCE: 18

Ile Ser Asn Pro Glu Tyr Leu
 1               5

<210> SEQ ID NO 19
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 19

Val Leu Ala Asp Asn Pro Ala Tyr Arg Ser Ala
 1               5                  10

<210> SEQ ID NO 20
<211> LENGTH: 14
<212> TYPE: PRT
<213> ORGANISM: phosphotyrosine binding domain
<220> FEATURE:
<221> NAME/KEY: MOD_RES
<222> LOCATION: (9)
```

-continued

<223> OTHER INFORMATION: Phosphorylated at Tyr

<400> SEQUENCE: 20

Ala Leu Leu Leu Ser Asn Pro Ala Tyr Arg Leu Leu Leu Ala
 1               5                  10

<210> SEQ ID NO 21
<211> LENGTH: 18
<212> TYPE: PRT
<213> ORGANISM: phosphotyrosine binding domain
<220> FEATURE:
<221> NAME/KEY: MOD_RES
<222> LOCATION: (11)
<223> OTHER INFORMATION: Phosphorylated at Tyr in position number 11

<400> SEQUENCE: 21

Gly Pro Leu Tyr Ala Ser Ser Asn Pro Glu Tyr Leu Ser Ala Ser Asp
 1               5                  10                  15
Val Phe

<210> SEQ ID NO 22
<211> LENGTH: 15
<212> TYPE: PRT
<213> ORGANISM: phosphotyrosine binding domain
<220> FEATURE:
<221> NAME/KEY: MOD_RES
<222> LOCATION: (9)
<223> OTHER INFORMATION: Phosphorylated at Tyr

<400> SEQUENCE: 22

Pro Val Ser Val Asp Asn Pro Glu Tyr Leu Leu Asn Ala Gln Lys
 1               5                  10                  15

<210> SEQ ID NO 23
<211> LENGTH: 15
<212> TYPE: PRT
<213> ORGANISM: phosphotyrosine binding domain
<220> FEATURE:
<221> NAME/KEY: MOD_RES
<222> LOCATION: (9)
<223> OTHER INFORMATION: Phosphorylated at Tyr

<400> SEQUENCE: 23

Leu Ser Leu Leu Ser Asn Pro Thr Tyr Ser Val Met Arg Ser Lys
 1               5                  10                  15

<210> SEQ ID NO 24
<211> LENGTH: 18
<212> TYPE: PRT
<213> ORGANISM: phosphotyrosine binding domain
<220> FEATURE:
<221> NAME/KEY: MOD_RES
<222> LOCATION: (12)
<223> OTHER INFORMATION: Phosphorylated at Tyr

<400> SEQUENCE: 24

Val Ser Ser Leu Asn Glu Met Ile Asn Pro Asn Tyr Ile Gly Met Gly
 1               5                  10                  15
Pro Phe

<210> SEQ ID NO 25
<211> LENGTH: 20
<212> TYPE: PRT
<213> ORGANISM: phosphotyrosine binding domain
<220> FEATURE:
<221> NAME/KEY: MOD_RES
<222> LOCATION: (14)
<223> OTHER INFORMATION: Phosphorylated at Tyr

```
<400> SEQUENCE: 25

Leu Leu Leu Thr Lys Pro Glu Met Phe Glu Asn Pro Leu Tyr Gly Ser
 1               5                  10                  15

Val Ser Ser Phe
            20

<210> SEQ ID NO 26
<211> LENGTH: 10
<212> TYPE: PRT
<213> ORGANISM: phosphotyrosine binding domain
<220> FEATURE:
<221> NAME/KEY: MOD_RES
<222> LOCATION: (6)
<223> OTHER INFORMATION: Phosphorylated at Tyr
<220> FEATURE:
<221> NAME/KEY: PEPTIDE
<222> LOCATION: (1)..(10)
<223> OTHER INFORMATION: other - cyclic

<400> SEQUENCE: 26

Ile Glu Asn Pro Gln Tyr Phe Ser Pro Gly
 1               5                  10

<210> SEQ ID NO 27
<211> LENGTH: 13
<212> TYPE: PRT
<213> ORGANISM: phosphotyrosine binding domain
<220> FEATURE:
<221> NAME/KEY: MOD_RES
<222> LOCATION: (7)
<223> OTHER INFORMATION: Phosphorylated at Tyr
<220> FEATURE:
<221> NAME/KEY: PEPTIDE
<222> LOCATION: (1)..(13)
<223> OTHER INFORMATION: other - cyclic

<400> SEQUENCE: 27

Ile Ile Glu Asn Pro Gln Tyr Phe Ser Asp Ala Pro Gly
 1               5                  10

<210> SEQ ID NO 28
<211> LENGTH: 14
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr
<220> FEATURE:
<221> NAME/KEY: PEPTIDE
<222> LOCATION: (1)..(14)
<223> OTHER INFORMATION: other - cyclic

<400> SEQUENCE: 28

His Ile Ile Glu Asn Pro Gln Tyr Phe Ser Asp Ala Pro Gly
 1               5                  10

<210> SEQ ID NO 29
<211> LENGTH: 10
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr
<220> FEATURE:
<221> NAME/KEY: PEPTIDE
<222> LOCATION: (1)..(10)
<223> OTHER INFORMATION: other - cyclic
```

<400> SEQUENCE: 29

Cys Ile Ile Glu Asn Pro Gln Tyr Phe Cys
 1               5                  10

<210> SEQ ID NO 30
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 30

Tyr Ala Ser Ser Asn Pro Glu Tyr Leu Ser Ala
 1               5                  10

<210> SEQ ID NO 31
<211> LENGTH: 11
<212> TYPE: PRT
<213> ORGANISM: phosphotyrosine binding domain
<220> FEATURE:
<221> NAME/KEY: MOD_RES
<222> LOCATION: (9)
<223> OTHER INFORMATION: Phosphorylated at Tyr

<400> SEQUENCE: 31

His Ala Ser Glu Asn Pro Gln Tyr Phe Ser Asp
 1               5                  10

<210> SEQ ID NO 32
<211> LENGTH: 4
<212> TYPE: PRT
<213> ORGANISM: phosphotyrosine binding domain
<220> FEATURE:
<221> NAME/KEY: MOD_RES
<222> LOCATION: (4)
<223> OTHER INFORMATION: Phosphorylated at Tyr

<400> SEQUENCE: 32

Asn Pro Glu Tyr
 1

<210> SEQ ID NO 33
<211> LENGTH: 6
<212> TYPE: PRT
<213> ORGANISM: phosphotyrosine binding domain

<400> SEQUENCE: 33

Phe Leu Val Arg Glu Ser
 1               5

<210> SEQ ID NO 34
<211> LENGTH: 6
<212> TYPE: PRT
<213> ORGANISM: phosphotyrosine binding domain

<400> SEQUENCE: 34

Tyr Leu Val Arg Tyr Met
 1               5

<210> SEQ ID NO 35
<211> LENGTH: 14
<212> TYPE: PRT
<213> ORGANISM: phosphotyrosine binding domain -continued

```
<400> SEQUENCE: 35

Cys Gly His Ile Ile Glu Asn Pro Gln Pro Tyr Phe Ser Asp
 1               5                  10

<210> SEQ ID NO 36
<211> LENGTH: 15
<212> TYPE: PRT
<213> ORGANISM: phosphotyrosine binding domain
<220> FEATURE:
<221> NAME/KEY: MOD_RES
<222> LOCATION: (9)
<223> OTHER INFORMATION: Phosphorylated at Tyr

<400> SEQUENCE: 36

Leu Ser Leu Leu Ser Asn Pro Thr Tyr Ser Val Met Arg Ser Lys
 1               5                  10                  15

<210> SEQ ID NO 37
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 37

His Ile Ile Glu Ala Pro Gln Tyr Phe Ser Asp
 1               5                  10

<210> SEQ ID NO 38
<211> LENGTH: 12
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 38

His Ile Ile Glu Asn Ala Gln Tyr Phe Ser Asp Pro
 1               5                  10

<210> SEQ ID NO 39
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 39

His Ile Ile Glu Asn Pro Gln Tyr Phe Ser Asp
 1               5                  10

<210> SEQ ID NO 40
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 40

His Ala Ala Glu Asn Pro Gln Tyr Phe Ser Asp
 1               5                  10
```

```
<210> SEQ ID NO 41
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 41

His Ala Ser Glu Asn Pro Gln Tyr Phe Ser Asp
 1               5                  10

<210> SEQ ID NO 42
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr in position number 8

<400> SEQUENCE: 42

Tyr Ala Ser Ser Asn Pro Glu Tyr Leu Ser Ala
 1               5                  10

<210> SEQ ID NO 43
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 43

His Ala Ile Glu Asn Pro Gln Tyr Phe Ser Asp
 1               5                  10

<210> SEQ ID NO 44
<211> LENGTH: 11
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr in position number 8

<400> SEQUENCE: 44

Tyr Ala Ile Ser Asn Pro Glu Tyr Leu Ser Ala
 1               5                  10

<210> SEQ ID NO 45
<211> LENGTH: 9
<212> TYPE: PRT
<213> ORGANISM: phosphotyrosine binding domain
<220> FEATURE:
<221> NAME/KEY: MOD_RES
<222> LOCATION: (6)
<223> OTHER INFORMATION: Phosphorylated at Tyr

<400> SEQUENCE: 45

Ile Glu Asn Pro Gln Tyr Phe Ser Asp
 1               5

<210> SEQ ID NO 46
<211> LENGTH: 10
```

```
<212> TYPE: PRT
<213> ORGANISM: phosphotyrosine binding domain
<220> FEATURE:
<221> NAME/KEY: MOD_RES
<222> LOCATION: (6)
<223> OTHER INFORMATION: Phosphorylated at Tyr
<220> FEATURE:
<221> NAME/KEY: PEPTIDE
<222> LOCATION: (1)..(10)
<223> OTHER INFORMATION: other - cyclic

<400> SEQUENCE: 46

Ile Glu Asn Pro Gln Tyr Phe Ser Pro Gly
  1               5                  10

<210> SEQ ID NO 47
<211> LENGTH: 10
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr
<220> FEATURE:
<221> NAME/KEY: PEPTIDE
<222> LOCATION: (1)..(10)
<223> OTHER INFORMATION: other - cyclic

<400> SEQUENCE: 47

Cys Ile Ile Glu Asn Pro Gln Tyr Phe Cys
  1               5                  10

<210> SEQ ID NO 48
<211> LENGTH: 4
<212> TYPE: PRT
<213> ORGANISM: phosphotyrosine binding domain
<220> FEATURE:
<221> NAME/KEY: MOD_RES
<222> LOCATION: (4)
<223> OTHER INFORMATION: Phosphorylated at Tyr
<220> FEATURE:
<221> NAME/KEY: PEPTIDE
<222> LOCATION: (1)..(4)
<223> OTHER INFORMATION: cyclic

<400> SEQUENCE: 48

Asn Pro Gln Tyr
  1

<210> SEQ ID NO 49
<211> LENGTH: 5
<212> TYPE: PRT
<213> ORGANISM: phosphotyrosine binding domain
<220> FEATURE:
<221> NAME/KEY: MOD_RES
<222> LOCATION: (4)
<223> OTHER INFORMATION: Phosphorylated at Tyr
<220> FEATURE:
<221> NAME/KEY: PEPTIDE
<222> LOCATION: (1)..(5)
<223> OTHER INFORMATION: cyclic

<400> SEQUENCE: 49

Asn Pro Gln Tyr Gly
  1               5

<210> SEQ ID NO 50
<211> LENGTH: 6
<212> TYPE: PRT
<213> ORGANISM: phosphotyrosine binding domain
<220> FEATURE:
```

```
<221> NAME/KEY: MOD_RES
<222> LOCATION: (4)
<223> OTHER INFORMATION: Phosphorylated at Tyr
<220> FEATURE:
<221> NAME/KEY: PEPTIDE
<222> LOCATION: (1)..(6)
<223> OTHER INFORMATION: cyclic

<400> SEQUENCE: 50

Asn Pro Gln Tyr Gly Gly
 1               5

<210> SEQ ID NO 51
<211> LENGTH: 27
<212> TYPE: PRT
<213> ORGANISM: phosphotyrosine binding domain

<400> SEQUENCE: 51

Arg Gln Ile Lys Ile Trp Phe Gln Asn Arg Arg Met Lys Trp Lys Lys
 1               5                  10                  15

His Ile Ile Glu Asn Pro Gln Tyr Phe Ser Asp
             20                  25

<210> SEQ ID NO 52
<211> LENGTH: 27
<212> TYPE: PRT
<213> ORGANISM: phosphotyrosine binding domain
<220> FEATURE:
<221> NAME/KEY: MOD_RES
<222> LOCATION: (24)
<223> OTHER INFORMATION: Phosphorylated at Tyr

<400> SEQUENCE: 52

Arg Gln Ile Lys Ile Trp Phe Gln Asn Arg Arg Met Lys Trp Lys Lys
 1               5                  10                  15

His Ile Ile Glu Asn Pro Gln Tyr Phe Ser Asp
             20                  25

<210> SEQ ID NO 53
<211> LENGTH: 30
<212> TYPE: PRT
<213> ORGANISM: phosphotyrosine binding domain

<400> SEQUENCE: 53

Ala Cys Ala Ala Ala Val Ala Leu Leu Pro Ala Val Leu Leu Ala Leu
 1               5                  10                  15

Leu Ala Pro His Ile Ile Glu Asn Pro Gln Tyr Phe Ser Asp
             20                  25                  30

<210> SEQ ID NO 54
<211> LENGTH: 30
<212> TYPE: PRT
<213> ORGANISM: phosphotyrosine binding domain
<220> FEATURE:
<221> NAME/KEY: MOD_RES
<222> LOCATION: (27)
<223> OTHER INFORMATION: Phosphorylated at Tyr

<400> SEQUENCE: 54

Ala Cys Ala Ala Ala Val Ala Leu Leu Pro Ala Val Leu Leu Ala Leu
 1               5                  10                  15

Leu Ala Pro His Ile Ile Glu Asn Pro Gln Tyr Phe Ser Asp
             20                  25                  30

<210> SEQ ID NO 55
```

-continued

```
<211> LENGTH: 15
<212> TYPE: PRT
<213> ORGANISM: phosphotyrosine binding domain
<220> FEATURE:
<221> NAME/KEY: MOD_RES
<222> LOCATION: (12)
<223> OTHER INFORMATION: Phosphorylated at Tyr

<400> SEQUENCE: 55

Ser Ser Cys Gly His Ile Ile Glu Asn Pro Gln Tyr Phe Ser Asp
 1               5                  10                  15

<210> SEQ ID NO 56
<211> LENGTH: 8
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr

<400> SEQUENCE: 56

His Ile Ile Glu Asn Pro Gln Tyr
 1               5

<210> SEQ ID NO 57
<211> LENGTH: 8
<212> TYPE: PRT
<213> ORGANISM: phosphotyrosine binding domain
<220> FEATURE:
<221> NAME/KEY: MOD_RES
<222> LOCATION: (8)
<223> OTHER INFORMATION: Phosphorylated at Tyr in position 8

<400> SEQUENCE: 57

Tyr Ala Ser Ser Asn Pro Glu Tyr
 1               5

<210> SEQ ID NO 58
<211> LENGTH: 307
<212> TYPE: PRT
<213> ORGANISM: phosphotyrosine binding domain

<400> SEQUENCE: 58

Met Asn Lys Leu Ser Gly Gly Gly Arg Arg Thr Arg Val Glu Gly
 1               5                  10                  15

Gly Gln Leu Gly Gly Glu Glu Trp Ile Arg His Gly Ser Phe Val Asn
                20                  25                  30

Lys Pro Thr Arg Gly Trp Leu His Pro Asn Asp Lys Val Met Gly Pro
            35                  40                  45

Gly Val Ser Tyr Leu Val Arg Tyr Met Gly Cys Val Glu Val Leu Gln
     50                  55                  60

Ser Met Arg Ala Leu Asp Phe Asn Ile Arg Thr Gln Val Thr Arg Glu
 65                  70                  75                  80

Ala Ile Ser Leu Val Cys Glu Ala Val Pro Gly Ala Lys Gly Ala Thr
                 85                  90                  95

Arg Arg Arg Lys Pro Cys Ser Arg Pro Leu Ser Ser Ile Leu Gly Arg
            100                 105                 110

Ser Asn Leu Lys Phe Ala Gly Met Pro Ile Thr Leu Thr Val Ser Thr
        115                 120                 125

Ser Ser Leu Asn Leu Met Ala Ala Asp Cys Lys Gln Ile Ile Ala Asn
    130                 135                 140

His His Met Gln Ser Ile Ser Phe Ala Ser Gly Gly Asp Pro Asp Thr
```

```
                145                 150                 155                 160
Ala Glu Tyr Val Ala Tyr Val Lys Asp Pro Val Asn Gln Arg Ala
                    165                 170                 175

Cys His Ile Leu Glu Cys Pro Glu Gly Leu Ala Gln Asp Val Ile Ser
                    180                 185                 190

Thr Ile Gly Gln Ala Phe Glu Leu Arg Phe Lys Gln Tyr Leu Arg Asn
                    195                 200                 205

Pro Pro Lys Leu Val Thr Pro His Asp Arg Met Ala Gly Phe Asp Gly
        210                 215                 220

Ser Ala Trp Asp Glu Glu Glu Glu Pro Pro Asp His Gln Tyr Tyr
225                 230                 235                 240

Asn Asp Phe Pro Gly Lys Glu Pro Leu Gly Gly Val Val Asp Met
                    245                 250                 255

Arg Leu Arg Glu Gly Ala Ala Pro Gly Ala Ala Arg Pro Thr Ala Pro
                260                 265                 270

Asn Ala Gln Thr Pro Ser His Leu Gly Ala Thr Leu Pro Val Gly Gln
                275                 280                 285

Pro Val Gly Gly Asp Pro Glu Val Arg Lys Gln Met Pro Pro Pro
        290                 295                 300

Pro Cys Pro
305

<210> SEQ ID NO 59
<211> LENGTH: 303
<212> TYPE: PRT
<213> ORGANISM: phosphotyrosine binding domain

<400> SEQUENCE: 59

Met Asn Lys Leu Ser Gly Gly Gly Arg Arg Thr Arg Val Glu Gly
  1               5                  10                  15

Gly Gln Leu Gly Gly Glu Glu Trp Ile Arg His Gly Ser Phe Val Asn
                    20                  25                  30

Lys Pro Thr Arg Gly Trp Leu His Pro Asn Asp Lys Val Met Gly Pro
                35                  40                  45

Gly Val Ser Tyr Leu Val Arg Tyr Met Gly Cys Val Glu Val Leu Gln
        50                  55                  60

Ser Met Arg Ala Leu Asp Phe Asn Ile Arg Thr Gln Val Thr Arg Glu
65                  70                  75                  80

Ala Ile Ser Leu Val Cys Glu Ala Val Pro Gly Ala Lys Gly Ala Thr
                    85                  90                  95

Arg Arg Arg Lys Pro Cys Ser Arg Pro Leu Ser Ser Ile Leu Gly Arg
                100                 105                 110

Ser Asn Leu Lys Phe Ala Gly Met Pro Ile Thr Leu Thr Val Ser Thr
            115                 120                 125

Ser Ser Leu Asn Leu Met Ala Ala Asp Cys Lys Gln Ile Ile Ala Asn
        130                 135                 140

His His Met Gln Ser Ile Ser Phe Ala Ser Gly Gly Asp Pro Asp Thr
145                 150                 155                 160

Ala Glu Tyr Val Ala Tyr Val Lys Asp Pro Val Asn Gln Arg Ala
                    165                 170                 175

Cys His Ile Leu Glu Cys Pro Glu Gly Leu Ala Gln Asp Val Ile Ser
                    180                 185                 190

Thr Ile Gly Gln Ala Phe Glu Leu Arg Phe Lys Gln Tyr Leu Arg Asn
                    195                 200                 205
```

```
Pro Pro Lys Leu Val Thr Pro His Asp Arg Met Ala Gly Phe Asp Gly
    210                 215                 220

Ser Ala Trp Asp Glu Glu Glu Glu Pro Pro Asp His Gln Tyr Tyr
225                 230                 235                 240

Asn Asp Phe Pro Gly Lys Glu Pro Pro Leu Gly Gly Val Val Asp Met
                    245                 250                 255

Arg Leu Arg Glu Gly Ala Ala Arg Pro Thr Leu Pro Ser Ala Gln Met
                260                 265                 270

Ser Ser His Leu Gly Ala Thr Leu Pro Ile Gly Gln His Ala Ala Gly
            275                 280                 285

Asp His Glu Val Arg Lys Gln Met Phe Leu Pro Pro Pro Cys Pro
        290                 295                 300
```

<210> SEQ ID NO 60
<211> LENGTH: 259
<212> TYPE: PRT
<213> ORGANISM: phosphotyrosine binding domain

<400> SEQUENCE: 60

```
Met Pro Lys Asn Gly Asp Ala Gly Gly Arg Ser Gly Ser Gly Thr Ile
 1               5                  10                  15

Ser Asp Gly Cys Ile Tyr Pro Asp Asp Val Ile Met Gly Val Gly Val
                20                  25                  30

Ala Phe Asn Val Arg Tyr Thr Gly Cys Val Glu Val Lys Thr Ser Met
            35                  40                  45

Lys Ser Leu Asp Phe Glu Ile Arg Thr Gln Leu Ala Arg Glu Cys Ile
    50                  55                  60

Asn Arg Val Cys Glu Ala Ala Gly Leu Lys Ser Ala Gly Lys Arg Arg
65                  70                  75                  80

Leu Thr Asn Phe Ile Ser Asp Arg Pro Ser Met Gln His Ala Gly Thr
                85                  90                  95

Asn Ile Ile Ile Asn Val Ser Ser Arg Ala Leu Ser Leu Ser Asn Val
            100                 105                 110

Glu Thr Gly Glu Val Ile Ala Asn His Asn Met Pro Arg Ile Ser Phe
    115                 120                 125

Ala Ser Gly Gly Asp Asn Asp Thr Leu Asp Phe Leu Ala Tyr Ile Ala
130                 135                 140

Lys Asn Glu Asp Glu Trp Arg Ala Cys Tyr Val Leu Glu Cys Ala Gly
145                 150                 155                 160

Gly Gln Ser Glu Asp Leu Ile Val Thr Ile Gly Lys Ala Phe Ala Leu
                165                 170                 175

Arg Phe Asn Ala Leu Ser Arg Leu Asn Asp Pro Ser Ala Asp Cys Asn
            180                 185                 190

Ile Asn Gln Ser Cys Lys Glu Asn Val Lys Glu Tyr Tyr Asn Asp Leu
    195                 200                 205

Pro Asn Lys Leu Pro Pro Glu Val Pro Glu Pro Gln Gln Gln Gln Val
210                 215                 220

Gln Gln Pro Leu His Pro His Ala Pro Arg Val Ala Gln Leu Asn Leu
225                 230                 235                 240

Lys Lys Pro Arg Asp Arg Leu Ser Ser Asn Leu Ile Asp Leu Asn Ser
                245                 250                 255

Pro Pro Pro
```

PEPTIDE INHIBITORS OF A PHOSPHOTYROSINE-BINDING DOMAIN CONTAINING PROTEIN

CROSS-REFERENCE TO RELATED APPLICATIONS

This application is a 371 of PCT/US96/17080, filed Oct. 24, 1996, which claims the benefit under Title 35, United States Code § 119(e) of Provisional application Ser. Nos. 60/005,944, 60/010,384, and 60/011,799 filed Oct. 27, 1995, Jan. 22, 1996, and Feb. 20, 1996, respectively.

FIELD OF THE INVENTION

The invention relates to peptides which interfere with the interaction of a phosphotyrosine-binding (PTB) domain containing protein with a PTB domain binding site; and, uses of the peptides.

BACKGROUND OF THE INVENTION

Shc is a member of a group of proteins that are collectively known as adaptor proteins. These adaptors, which are composed of protein-protein interaction domains such as the Src-homology 2 (SH2) and Src-homology 3 (SH3) domains, mediate protein-protein interactions that are important for signal transduction downstream of growth factor and cytokine receptors (Pawson, 1995). Shc has been shown to bind to a wide variety of activated growth factor and cytokine receptors. Shc was cloned from a human cDNA library in a screen for SH2 domain-containing proteins (Pelicci et al., 1992); Shc homologs in mouse (mShc) and drosophila (dShc) have also been cloned (Lai et al., 1995). Three proteins are encoded by the shc gene that differ from each other only in their amino-terminus (Lai et al., 1995; Pelicci et al., 1992). Overexpression of Shc results in cellular transformation of NIH3T3 fibroblasts and Ras-dependent neurite outgrowth of PC12 cells, suggesting that Shc plays an important role in signal transduction leading to DNA synthesis and cell division or differentiation (Pelicci et al., 1992; Rozakis-Adcock et al., 1992).

Shc contains an amino-terminal phosphotyrosine-binding (PTB) domain, a central Pro-rich region that contains the principal tyrosine phosphorylation site at Tyr 317, and an SH2 domain at its carboxy-terminus. The PTB domain, which is highly conserved in Shc-related proteins, was recently identified based on its ability to bind to phosphotyrosine-containing proteins (Blaikie et al., 1994; Kavanaugh and Williams, 1994; van der Geer et al., 1995). It recognizes phosphotyrosine present within the sequence Asn-Pro-X-P.Tyr and differs from SH2 domains that recognize phosphotyrosine in the context of carboxy-terminal residues (Kavanaugh et al., 1995; van der Geer et al., 1995). The Shc SH2 domain recognizes phosphotyrosine within the sequence P.Tyr-Glu/Leu/Ile/Tyr-X-Leu/Ile/Met (Songyang et al., 1994).

Shc becomes phosphorylated on tyrosine following stimulation with a wide variety of growth factors and cytokines (Burns et al., 1993; Crowe et al., 1994; Cutler et al., 1993; Lanfrancone et al., 1995; Pelicci et al., 1992; Pronk et al., 1993; Ravichandran et al., 1993; Segatto et al., 1993; Yokote et al., 1994). Tyrosine phosphorylation of Shc is essential for its interaction with the Grb2-Sos complex, which may provide a mechanism for Ras activation (Buday and Downward, 1993; Crowe et al., 1994; Egan et al., 1993; Gale et al., 1993; Li et al., 1993; Rozakis-Adcock et al., 1993; Rozakis-Adcock et al., 1992; Salcini et al., 1994). Shc has also been shown to bind physically to activated growth factor and cytokine receptors. Several growth factor receptors that had previously been shown to bind to Shc upon activation contain tyrosine phosphorylation sites present within the sequence Asn-Pro-X-P.Tyr, consistent with the notion that it is the PTB domain that mediates Shc's interaction with these proteins (Campbell et al., 1994; van der Geer and Pawson, 1995). Furthermore, the Shc PTB domain has been shown to bind to the activated nerve growth factor (NGF) receptor, the activated epidermal growth factor (EGF) receptor, polyoma middle T antigen, and to a 145 kDa protein that becomes phosphorylated on tyrosine in PDGF stimulated cells (Blaikie et al., 1994; Kavanaugh and Williams, 1994; van der Geer et al., 1995). The NGF receptor contains a single Shc-binding site at Tyr 490 that is present within a Asn-Pro-X-Tyr motif (Obermeier et al., 1994; Stephens et al., 1994). NGF receptors that have been mutated at Tyr 490 lack the ability to interact with Shc in vivo or with the PTB domain in vitro (Stephens et al., 1994). Phosphotyrosine-containing peptides based on the Shc binding site in middle T antigen, which is also present within an Asn-Pro-X-P.Tyr motif, compete with the NGF and EGF receptors for binding to the PTB domain (van der Geer et al., 1995).

SUMMARY OF THE INVENTION

The present inventors have identified the residues within the Asn-Pro-X-P.Tyr motif of phosphotyrosine-containing proteins (e.g. growth activated growth factors and cytokine receptors) that mediate the binding of the proteins to signalling proteins containing PTB domains. In particular, the present inventors found that the Asn and the phosphotyrosine residues within the Asn-Pro-X-P.Tyr motif of the phosphotyrosine-containing proteins mediate their binding to the PTB domain of Shc. The present inventors also found that an aliphatic residue that is five or six residues amino-terminal to the phosphotyrosine is required for binding. This aliphatic residue is missing from the insulin receptor autophosphorylation site which is unable to form a stable complex with Shc. The present inventors also analyzed the Shc PTB domain by in vitro mutagenesis and an evolutionarily conserved Arg residue was identified that is important for PTB binding to its ligands.

Broadly stated the present invention relates to a peptide of the formula I

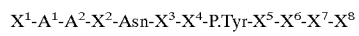

wherein $X^1$ represents Lys, Arg, His, Ser, Thr, Tyr, Asn, Leu, Val, or Glu, $A^1$ represents Trp, Leu, Ala, Ser, Ile, Glu, Met, Gly, Cys, Phe, Pro, or Val, and $A^2$ represents Ala, Val, Leu, Ile, Ser, Met, Phe, Gly, Cys, Trp, or Pro, $X^2$ represents Glu, Asn, Tyr, Thr, Ser, Asp, or Ile, $X^3$ represents Pro, Met, Trp, Phe, Ala, Lys, Val, Leu, Ile, Gly, or Cys, $X^4$ represents Leu, Ala, Glu, Gln, Asp, Asn, Tyr, Thr, or Ser, $X^5$ represents Phe, Trp, Pro, Leu, Ala, Val, Ile, Gly, Cys, Met, Arg or Ser, $X^6$ represents Ser, Thr, Tyr, Asn, Glu, Met, Ala, Leu, Val, or Gly, $X^7$ represents Asp, Glu, Ala, Val, Leu, Ile, Gly, Cys, Phe, Trp, Met, Pro, Ser, or Asn, and $X^8$ which may be present or absent represents Phe, Trp, Pro, Leu, Ala, Val, Ile, Gly, Cys, Met, Asp, Ser, or Arg, which interferes with the interaction of a PTB domain containing protein with a PTB domain binding site.

In an embodiment of the present invention a peptide of the formula I is provided:

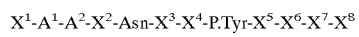

wherein X¹ represents His, Ser, Thr, Tyr, Asn, Leu, Val, or Glu, X² represents Glu, Ser, Asp, or Ile, X³ represents Pro or Lys, X⁴ represents Leu, Ala, Glu, Gln, Asn, or Thr, X⁵ represents Phe, Leu, Ile, Gly, Arg, or Ser, X⁶ represents Ser, Thr, Met, Ala, Leu, Val, or Gly, X⁷ represents Asp, Ala, Val, Leu, Met, Ser, or Asn, X⁸ which may be present or absent, represents Leu, Ala, Gly, Asp, Ser, or Arg, A¹ represents Trp, Leu, Ala, Ser, Ile, Glu, Met, or Val, and A² represents Ala, Val, Leu, Ile, Ser, Met, or Phe, which interferes with the interaction of a PTB domain containing protein with a PTB domain binding site.

In another embodiment of the invention a peptide of the formula Ia is provided

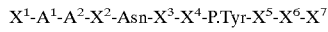

wherein X¹ represents Lys, Arg, His, preferably His, X² represents Glu, Asn, Tyr, Thr, Ser, preferably Glu, X³, represents Pro, Met, Trp, Phe, Ala, Val, Leu, Ile, Gly, Cys, preferably Pro, X⁴ represents Gln, Asp, Asn, Tyr, Thr, Ser, preferably Gln, X⁵ represents Phe, Trp, Pro, Leu, Ala, Val, Ile, Gly, Cys, Met, preferably Phe, X⁶ represents Ser, Thr, Tyr, Asn, Glu, preferably Ser, X⁷ represents Asp, Glu, preferably Asp, and one of A¹ and A² represents Ile and the other of A¹ and A² represents Ile or Ala, preferably A¹ represents Ala and A² represents Ile, which interferes with the interaction of a PTB domain containing protein with a PTB domain binding site.

In still another embodiment of the invention a peptide of the formula Ia is provided

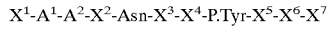

wherein X¹ represents Ser, Thr, Tyr, Asn or Glu, preferably Tyr, X² represents Glu, Asn, Tyr, Thr, Ser, preferably Ser, X³ represents Pro, Met, Trp, Phe, Ala, Val, Leu, Ile, Gly, Cys, preferably Pro, X⁴ represents Glu, Asp, preferably Glu, X⁵ represents Phe, Trp, Pro, Leu, Ala, Val, Ile, Gly, Cys, Met preferably Leu, X⁶ represents Ser, Thr, Tyr, Asn, Glu, preferably Ser, X⁷ represents Ala, Val, Leu, Ile, Gly, Cys, Phe, Trp, Met, Pro, preferably Ala, and one of A¹ and A² represents Ile and the other of A¹ and A² represents Ala, Val, Leu, Ile, Gly, Cys, Phe, Trp, Met or Pro, which interferes with the interaction of a PTB domain containing protein with a PTB domain binding site.

The invention also relates to truncations and analogs of the peptides of the invention.

The invention also relates to the use of a peptide of the formula I or Ia to interfere with the interaction of a PTB domain containing protein with a PTB domain binding site; and, pharmaceutical compositions for inhibiting the interaction of a PTB domain containing protein with a PTB domain binding site.

Further, the invention relates to a method of modulating the interaction of a PTB domain containing protein with a PTB domain binding site comprising changing the amino acid Arg at position 175 in the PTB domain containing protein. The invention still further relates to a method for modulating the interaction of an insulin receptor with insulin receptor substrate 1 (IRS-1) or Shc comprising incorporating a large aliphatic amino acid at amino acids −5 or −6 amino terminal to the P.Tyr in the motif Asn-Pro-X-P.Tyr in the PTB domain of the insulin receptor.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 7 shows the amino acid sequences of PTB binding domains of mammalian and Drosophila Shc homologues (SEQ ID NOs:58, 59 and 60);

FIG. 14a is a bar graph showing proliferation of SupM2 cells treated with peptides of the invention;

FIG. 14b is a bar graph showing proliferation of SupM2 cells treated with peptides of the invention;

FIG. 16a is an immunoblot showing activated MAPK on PC12 cells treated with peptides of the invention; and FIG. 16b is an immunoblot showing activated MAPK on PC12 cells treated with peptides of the invention.

DETAILED DESCRIPTION OF THE INVENTION

Figure 1A:
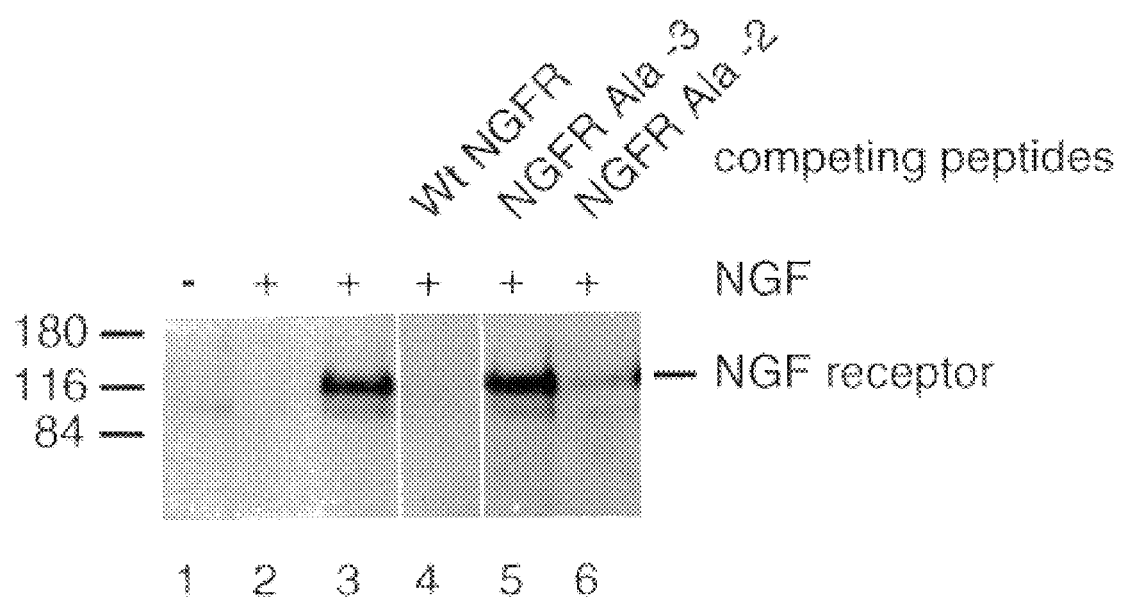
FIG. 1A is an immunoblot showing P.Tyr-containing proteins bound to GST (lane 2) and GST Shc PTB (lanes 1, 3–6) fusion proteins immobilized on glutathione-agarose after incubation with lysates from control (lane 1) and NGF-stimulated (lanes 2–7) cells in the absence (lane 1–3) and presence of Wt (lane 4) and mutant (lanes 5 and 6) competing P.Tyr containing peptides, based on the sequence around Tyr 490 the Shc PTB domain binding site in the NGF receptor.

The following standard abbreviations for the amino acid residues are used throughout the specification: A, Ala-alanine; C, Cys-cysteine; D, Asp-aspartic acid; E, Glu-glutamic acid; F, Phe-phenylalanine; G, Gly-glycine; H, His-histidine; I, Ile-isoleucine; K, Lys-lysine; L, Leu-leucine; M, Met-methionine; N, Asn-asparagine; P, Pro-proline; Q, Gln-glutamine; R, Arg-arginine; S, Ser-serine; T, Thr-threonine; V, Val-valine; W, Trp-tryptophan; Y, Tyr-tyrosine; and p.Y., P.Tyr-phosphotyrosine.

As mentioned previously, the present invention relates to a peptide of the formula I

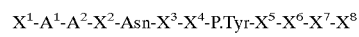

$$X^1\text{-}A^1\text{-}A^2\text{-}X^2\text{-}Asn\text{-}X^3\text{-}X^4\text{-}P.Tyr\text{-}X^5\text{-}X^6\text{-}X^7\text{-}X^8 \qquad I$$

wherein $X^1$ represents Lys, Arg, His, Ser, Thr, Tyr, Asn, Leu, Val, or Glu, $A^1$ represents Trp, Leu, Ala, Ser, Ile, Glu, Met, Gly, Cys, Phe, Pro, or Val, and $A^2$ represents Ala, Val, Leu, Ile, Ser, Met, Phe, Gly, Cys, Trp, or Pro, $X^2$ represents Glu, Asn, Tyr, Thr, Ser, Asp, or Ile, $X^3$ represents Pro, Met, Trp, Phe, Ala, Lys, Val, Leu, Ile, Gly, or Cys, $X^4$ represents Leu, Ala, Glu, Gln, Asp, Asn, Tyr, Thr, or Ser, $X^5$ represents Phe, Trp, Pro, Leu, Ala, Val, Ile, Gly, Cys, Met, Arg or Ser, $X^6$ represents Ser, Thr, Tyr, Asn, Glu, Met, Ala, Leu, Val, or Gly, $X^7$ represents Asp, Gin, Ala, Val, Leu, Ile, Gly, Cys, Phe, Trp, Met, Pro, Ser, or Asn, and $X^8$ which may be present or absent represents Phe, Trp, Pro, Leu, Ala, Val, Ile, Gly, Cys, Met, Asp, Ser, or Arg, which interferes with the interaction of a PTB domain containing protein with a PTB domain binding site.

In an embodiment of the present invention a peptide of the formula I is provided:

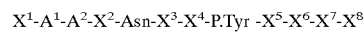

$$X^1\text{-}A^1\text{-}A^2\text{-}X^2\text{-}Asn\text{-}X^3\text{-}X^4\text{-}P.Tyr\ \text{-}X^5\text{-}X^6\text{-}X^7\text{-}X^8 \qquad I$$

wherein $X^1$ represents His, Ser, Thr, Tyr, Asn, Leu, Val, or Gin, $X^2$ represents Glu, Ser, Asp, or Ile, $X^3$ represents Pro or Lys, $X^4$ represents Leu, Ala, Glu, Gln Asn, or Thr, $X^5$ represents Phe, Leu, Ile, Gly, Arg, or Ser, $X^6$ represents Ser, Thr, Met, Ala, Leu, Val, or Gly, $X^7$ represents Asp, Ala, Val, Leu, Met, Ser, or Asn, $X^8$ which may be present or absent, represents Leu, Ala, Gly, Asp, Ser, or Arg, $A^1$ represents Trp, Leu, Ala, Ser, Ile, Gln, Met, or Val, and $A^2$ represents Ala, Val, Leu, Ile, Ser, Met, or Phe, which interferes with the interaction of a PTB domain containing protein with a PTB domain binding site.

In another embodiment of the invention a peptide of the formula Ia is provided

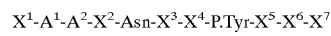

$$X^1\text{-}A^1\text{-}A^2\text{-}X^2\text{-}Asn\text{-}X^3\text{-}X^4\text{-}P.Tyr\text{-}X^5\text{-}X^6\text{-}X^7 \qquad Ia$$

wherein $X^1$ represents Lys, Arg, His, preferably His, $X^2$ represents Glu, Asn, Tyr, Thr, Ser, preferably Glu, $X^3$ represents Pro, Met, Trp, Phe, Ala, Val, Leu, Ile, Gly, Cys, preferably Pro, $X^4$ represents Gln, Asp, Asn, Tyr, Thr, Ser, preferably Gln, $X^5$ represents Phe, Trp, Pro, Leu, Ala, Val, Ile, Gly, Cys, Met, preferably Phe, $X^6$ represents Ser, Thr, Tyr, Asn, Gln, preferably Ser, $X^7$ represents Asp, Gin, preferably Asp, and one of $A^1$ and $A^2$ represents Ile and the other of $A^1$ and $A^2$ represents Ile or Ala, preferably $A^1$ represents Ala and $A^2$ represents Ile, which interferes with the interaction of a PTB domain containing protein with a PTB domain binding site.

In still another embodiment of the invention a peptide of the formula Ia is provided

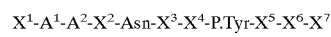

$$X^1\text{-}A^1\text{-}A^2\text{-}X^2\text{-}Asn\text{-}X^3\text{-}X^4\text{-}P.Tyr\text{-}X^5\text{-}X^6\text{-}X^7 \qquad Ia$$

wherein $X^1$ represents Ser, Thr, Tyr, Asn or Glu, preferably Tyr, $X^2$ represents Glu, Asn, Tyr, Thr, Ser, preferably Ser, $X^3$ represents Pro, Met, Trp, Phe, Ala, Val, Leu, Ile, Gly, Cys, preferably Pro, $X^4$ represents Glu, Asp, preferably Glu, $X^5$ represents Phe, Trp, Pro, Leu, Ala, Val, Ile, Gly, Cys, Met preferably Leu, $X^6$ represents Ser, Thr, Tyr, Asn, Glu, preferably Ser, $X^7$ represents Ala, Val, Leu, Ile, Gly, Cys, Phe, Trp, Met, Pro, preferably Ala, and one of $A^1$ and $A^2$ represents Ile and the other of $A^1$ and $A^2$ represents Ala, Val, Leu, Ile, Gly, Cys, Phe, Trp, Met or Pro, which interferes with the interaction of a PTB domain containing protein with a PTB domain binding site.

Preferred peptides of the invention include the following: His-Ile-Ile-Glu-Asn-Pro-Gln-P.Tyr-Phe-Ser-Asp; His-Ala-Ile-Glu-Asn-Pro-Gln-P.Tyr-Phe-Ser-Asp; His-Ile-Ala-Glu-Asn-Pro-Gln-P.Tyr-Phe-Ser-Asp; Ile-Ile-Glu-Asn-Pro-Gln-P.Tyr-Phe-Ser-Asp-Ala; Tyr-Ala-Ile-Ser-Asn-Pro-Glu-P.Tyr-Leu-Ser-Ala; Thr-Trp-Ile-Glu-Asn-Lys-Leu-P.Tyr-Gly-Met-Ser-Asp; Thr-Trp-Ile-Glu-Asn-Lys-Leu-P.Tyr-Gly-Thr-Ser-Asp; Leu-Leu-Leu-Ser-Asn-Pro-Ala-P.Tyr.-Arg-Leu-Leu-Leu; Tyr-Ala-Ser-Ser-Asn-Pro-Glu-P.Tyr-Leu-Ser-Ala-Ser; Val-Ser-Val-Asp-Asn-Pro-Glu-P.Tyr-Leu-Leu-Asn-Ala; Ser-Leu-Leu-Ser-Asn-Pro-Thr-P.Tyr-Ser-Val-Met-Arg; Asn-Glu-Met-Ile-Asn-Pro-Asn-P.Tyr-Ile-Gly-Met-Gly; and Glu-Met-Phe-Glu-Asn-Pro-Leu-P.Tyr-Gly-Ser-Val-Ser (SEQ. ID. NOS. 1–13 in the Sequence Listing).

In addition to full-length peptides of the formula I, truncations of the peptides which inhibit interaction of PTB domain containing proteins with PTB domain binding sites are contemplated in the present invention. Truncated peptides may comprise peptides of about 7 to 10 amino acid residues. In an embodiment of the invention the truncated peptide has the sequence $A^2-X^2-Asn-X^3-X^4$-P.Tyr or $A^2-X^2-Asn-X^3-X^4$-P.Tyr-$X^5$ wherein $A^2$, $X^2$, $X^3$, $X^4$, and $X^5$ are as defined above. In a preferred embodiment of the invention, the truncated peptide has the sequence Leu/Ile-$X^2$-Asn-Pro-$X^4$-P.Tyr, wherein $X^2$ represents Glu, Ser, Asp, or Ile, and $X^4$ represents Leu, Ala, Glu, Gln, Asn, or Thr. Examples of truncated peptides include Ile-Glu-Asn-Pro-Gln-P.Tyr-Phe; Ile-Glu-Asn-Pro-Gln-P.Tyr-Phe-Ser-Pro-Gly; Ala-Glu-Asn-Pro-Gln-P.Tyr-Phe; Ile-Glu-Asn-Pro-Gln-P.Tyr-Phe-Ser; Ile-Ser-Asn-Pro-Glu-P.Tyr-Leu; Val-Leu-Ala-Asp-Asn-Pro-Ala-P.Tyr-Arg-Ser-Ala (SEQ. ID. NOs. 14 to 19 in the Sequence Listing).

The truncated peptides may have an amino group (—NH$_2$), a hydrophobic group (for example, carbobenzoxyl, dansyl, or T-butyloxycarbonyl), an acetyl group, a 9-fluorenylmethoxy-carbonyl (PMOC) group, or a macromolecule including but not limited to lipid-fatty acid conjugates, polyethylene glycol, or carbohydrates at the amino terminal end. The truncated peptides may have a carboxyl group, an amido group, a T-butyloxycarbonyl group, or a macromolecule including but not limited to lipid-fatty acid conjugates, polyethylene glycol, or carbohydrates at the carboxy terminal end.

The peptides of the invention may also include analogs of the peptide of the Formula I, and/or truncations of the peptide, which may include, but are not limited to the peptide of the formula I containing one or more amino acid insertions, additions, or deletions, or both. Analogs of the peptide of the invention exhibit the activity characteristic of the peptide i.e. interference with the interaction of a PTB domain containing protein with a PTB domain binding site, and may further possess additional advantageous features such as increased bioavailability, stability, or reduced host immune recognition.

One or more amino acid insertions may be introduced into a peptide of the formula I preferably outside the sequence $A^2-X^2-Asn-X^3-X^4$-P.Tyr-$X^5$. For example, amino acid insertions may be made between $X^1$ and $A^1$ or between $X^5$ and $X^6$, or $X^6$ and $X^7$. Amino acid insertions may consist of a single amino acid residue or sequential amino acids.

One or more amino acids, preferably one to five amino acids, may be added to the right or left termini of a peptide of the invention. Examples of such analogs include Ala-Leu-Leu-Leu-Ser-Asn-Pro-Ala-P.Tyr.-Arg-Leu-Leu-Leu-Ala; Gly-Pro-Leu-Tyr-Ala-Ser-Ser-Asn-Pro-Glu-P.Tyr-Leu-Ser-Ala-Ser-Asp-Val-Phe; Pro-Val-Ser-Val-Asp-Asn-Pro-Glu-P.Tyr-Leu-Leu-Asn-Ala-Gln-Lys; Leu-Ser-Leu-Leu-Ser-Asn-Pro-Thr-P.Tyr-Ser-Val-Met-Arg-Ser-Lys; Val-Ser-Ser-Leu-Asn-Glu-Met-Ile-Asn-Pro-Asn-P.Tyr-Ile-Gly-Met-Gly-Pro-Phe; and Leu-Leu-Leu-Thr-Lys-Pro-Glu-Met-Phe-Glu-Asn-Pro-Leu-P.Tyr-Gly-Ser-Val-Ser-Ser-Phe (SEQ. ID. NOs. 20 to 25 in the Sequence Listing).

Deletions may consist of the removal of one or more amino acids, or discrete portions from the peptide sequence preferably outside the $A^2-X^2-Asn-X^3-X^4$-P.Tyr sequence. The deleted amino acids may or may not be contiguous. The lower limit length of the resulting analog with a deletion mutation is about 7 amino acids.

It is anticipated that if amino acids are inserted or deleted in sequences outside the $A^2-X^2-Asn-X^3-X^4$-P.Tyr sequence that the resulting analog of the peptide will exhibit the activity of a peptide of the invention.

Cyclic derivatives of the peptides of the invention are also part of the present invention. Cyclization may allow the peptide to assume a more favorable conformation for association with a PTB domain containing protein. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466–8467. The side chains of P.Tyr and Asn may be linked to form cyclic peptides. The components that form the bonds may be side chains of amino acids, non-amino acid components or a combination of the two.

Preferred cyclic peptides of the invention include cyclo-(Ile-Glu-Asn-Pro-Gln-P.Tyr-Phe-Ser-Pro-Gly, and cyclo-(Ile-Ile-Glu-Asn-Pro-Gln-P.Tyr-Phe-Ser-Asp-Ala-Pro-Gly) (SEQ. ID. NOs. 26 to 27 in the Sequence Listing) where the amino group of isoleucine and the carboxyl group of glycine form a peptide bond; cyclo-(His-Ile-Ile-Glu-Asn-Pro-Gln-P.Tyr-Phe-Ser-Asp-Ala-Pro-Gly) (SEQ. ID. NO. 28 in the Sequence Listing) where the amino group of histidine and the carboxyl group of glycine form a peptide bond; and Cys-Ile-Ile-Glu-Asn-Pro-Gln-P.Tyr-Phe-Cys (SEQ. ID. NO. 29 in the Sequence Listing) having a disulphide bond between the two cysteine residues.

In an embodiment of the invention, cyclic peptides are contemplated that have a beta-turn in the right position. Beta-turns may be introduced into the peptides of the invention by adding the amino acids Pro-Gly at the right position. An example of such a cyclic peptide is a peptide of the invention with an Ile in the left position (i.e. a terminal $A^1$ or $A^2$ is Ile) and the amino acids Pro-Gly at the right position. The amino group of the Ile and the carboxyl group of the Gly form a peptide bond resulting in a cyclic peptide. The 3D structure of the cyclic peptide is similar to the original structure of the PTB binding site of TrkA.

The following is an example of a cyclic peptide that has a beta-turn in the right position: cyclo-(Ile-Glu-Asn-Pro-Gln-P.Tyr-Phe-Ser-Pro-Gly) (SEQ. ID. NO. 26 in the Sequence Listing). In this peptide, Asn-Pro-Gln-P.Tyr [aa 3–6 of SEQ ID NO:26] take a native beta-turn, Ser-Pro-Gly-Ile [aa 8, 9, 10, and 1 of the cyclopeptide of SEQ ID NO:26] make another beta-turn on the other side, and the central part adopts an antiparallel beta-sheet. A beta-sheet has two faces, and the peptide binds to the PTB domain with the face on which the side chains of Ile, Asn, and P.Tyr extend. The side chains of Glu and Phe are on the other face, and may not affect the binding affinity. It may be possible to control the binding specificity by the side-chain of Gln as this side chain may contact the PTB domain.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The invention also includes a peptide conjugated with a selected peptide, protein, or a selectable marker (see below) to produce fusion proteins. For example, a peptide of the invention may be conjugated with a peptide which facilitates entry into cells.

The peptides of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

The peptides of the invention may be prepared using recombinant DNA methods. Accordingly, nucleic acid molecules which encode a peptide of the invention may be incorporated in a known manner into an appropriate expression vector which ensures good expression of the peptide. Possible expression vectors include but are not limited to cosmids, plasmids, or modified viruses so long as the vector is compatible with the host cell used. The expression vectors contain a nucleic acid molecule encoding a peptide of the invention and the necessary regulatory sequences for the transcription and translation of the inserted protein-sequence. Suitable regulatory sequences may be obtained from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Other sequences, such as an origin of replication, additional DNA restriction sites, enhancers, and sequences conferring inducibility of transcription may also be incorporated into the expression vector.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

The recombinant expression vectors may also contain genes which encode a fusion portion which provides increased expression of the recombinant peptide; increased solubility of the recombinant peptide; and/or aid in the purification of the recombinant peptide by acting as a ligand in affinity purification. For example, a proteolytic cleavage site may be inserted in the recombinant peptide to allow separation of the recombinant peptide from the fusion portion after purification of the fusion protein. Examples of fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors may be introduced into host cells to produce a transformant host cell. Transformant host cells include prokaryotic and eukaryotic cells which have been transformed or transfected with a recombinant expression vector of the invention. The terms "transformed with", "transfected with", "transformation" and "transfection" are intended to include the introduction of nucleic acid (e.g. a vector) into a cell by one of many techniques known in the art. For example, prokaryotic cells can be transformed with nucleic acid by electroporation or calcium-chloride mediated transformation. Nucleic acid can be introduced into mammalian cells using conventional techniques such as calcium phosphate or calcium chloride co-precipitation, DEAE-dextran-mediated transfection, lipofectin, electroporation or microinjection. Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the peptides of the invention may be expressed in bacterial cells such as $E.$ $coli$, insect cells (using baculovirus), yeast cells or mammalian cells. Other suitable host cells can be found in Goeddel, Gene Expression Technology: Methods in Enzymology 185, Academic Press, San Diego, Calif. (1991).

The peptides of the invention may be tyrosine phosphorylated using the method described in Reedijk et al. (The EMBO Journal 11(4): 1365, 1992). For example, tyrosine phosphorylation may be induced by infecting bacteria harbouring a plasmid containing a nucleotide sequence encoding a peptide of the invention, with a λgt11 bacteriophage encoding the cytoplasmic domain of the Elk tyrosine kinase as a LacZ-Elk fusion. Bacteria containing the plasmid and bacteriophage as a lysogen are isolated. Following induction of the lysogen, the expressed peptide becomes phosphorylated by the Elk tyrosine kinase.

The peptides of the invention may also be prepared by chemical synthesis using techniques well known in the chemistry of proteins such as solid phase synthesis (Merrifield, 1964, J. Am. Chem. Assoc. 85: 2149–2154) or synthesis in homogenous solution (Houbenweyl, 1987, Methods of Organic Chemistry, ed. E. Wansch, Vol. 15 I and II, Thieme, Stuttgart). By way of example, the peptides may be synthesized using 9-fluorenyl methoxycarbonyl (Fmoc) solid phase chemistry with direct incorporation of phosphotyrosine as the N-fluorenylmethoxy-carbonyl-O-dimethyl phosphono-L-tyrosine derivative.

N-terminal or C-terminal fusion proteins comprising a peptide of the invention conjugated with other molecules may be prepared by fusing, through recombinant techniques, the N-terminal or C-terminal of the peptide, and the sequence of a selected protein or selectable marker with a desired biological function. The resultant fusion proteins contain the peptide fused to the selected protein or marker protein as described herein. Examples of proteins which may be used to prepare fusion proteins include immunoglobulins, glutathione-S-transferase (GST), hemagglutinin (HA), and truncated myc.

The peptides of the invention may be used to prepare monoclonal or polyclonal antibodies. Conventional methods can be used to prepare the antibodies. As to the details relating to the preparation of monoclonal antibodies reference can be made to Goding, J. W., Monoclonal Antibodies: Principles and Practice, 2nd Ed., Academic Press, London, 1986. As discussed below, the antibodies may be used to identify proteins with PTB domain binding sites.

The peptides and antibodies specific for the peptides of the invention may be labelled using conventional methods with various enzymes, fluorescent materials, luminescent materials and radioactive materials. Suitable enzymes, fluorescent materials, luminescent materials, and radioactive material are well known to the skilled artisan. Labeled antibodies specific for the peptides of the invention may be used to screen for proteins with PTB domain binding sites, and labeled peptides of the invention may be used to screen for PTB domain containing proteins such as Shc.

The peptides of the invention interfere with the interaction of a PTB domain containing protein and a PTB domain binding site. The term "PTB domain containing protein" refers to a protein or peptide which comprises or consists of a PTB domain. A PTB domain is a region which is a domain of ~160 amino acids which was originally identified in Shc and Sck (Kavanaugh, V. M. Et al., 1995 Science, 268: 1177–1179; Bork, R P, and Margolis, B, Cell, Vol 80: 693–694, 1995; Craparo, A., et al., 1995, J. Biol. Chem. 270: 15639–15643; van der Geer, P., & Pawson, T., 1995, TIBS 20: 277–280; Batzer, A. G., et al., Mol. Cell. Biol. 1995, 15: 4403–4409; and Trub, T., et al., 1995, J. Biol. Chem. 270: 18205–18208; van der Geer et al., Current Biology 5(4): 404, 1995)). The PTB domain comprises residues 46 to 208 in the 52 kDa isoform of Shc. The sequences of several known PTB domains are aligned in FIG. 7. In FIG. 7, residues that are conserved within the sequences are shaded.

Examples of PTB domain containing proteins are mammalian Shc and Sck, IRS-1, and homologues of Shc including Drosophila Shc, and mouse Shc. Other proteins that contain homologous PTB domains have been identified using data base search methods (Bork, R. P., and Margolis, B. Cell, Vol 80: 693–694, 1995). PTB domain containing proteins may also be identified by screening a cDNA expression library with a protein containing a sequence with high affinity to PTB domains, i.e. a PTB domain binding sequence or a peptide of the invention which may be labeled. PTB domain containing proteins may also be screened using antibodies specific for the PTB domain. For example, a PTB domain that binds to the consensus sequence Leu/Ile-X-Asn-Pro-X-P.Tyr found in growth factors may be identified by screening a cDNA expression library with proteins based on the consensus sequence. PCR(Wilks, A. F., Proc. Natl. Acad. Sci. U.S.A. Vol. 86, pp. 1603–1607, March 1989) or low stringency screening (Hanks, S. K., Proc. Natl. Acad. Sci. U.S.A. Vol. 84, pp 388–392, January 1987) with the PTB domain specific probe can be used.

The term "PTB domain binding site" refers to a sequence with high affinity to PTB domains. PTB domain binding sequences have been identified in activated growth factors such as activated nerve growth factor receptor, activated epidermal growth factor (EGF) receptor, polyoma middle T antigen, and SHIP (Blaikie et al., 1994; Kavanaugh and Williams, 1994; van der Geer et al., 1995; Damen et al., 1996), ErbB2, ErbB3, TrkA, TrkB, TrkC, MCK10b, insulin receptor, IGF-1 receptor, and IL-4 receptor. PTB domain binding sites may be identified by screening with PTB domain containing proteins or with antibodies specific for the peptides of the invention.

The phrase "interfere with the interaction of" refers to the ability of the peptides of the invention to inhibit the binding of a PTB domain containing protein to a PTB domain binding site thereby affecting regulatory pathways that control gene expression, cell division, cytoskeletal architecture and cell metabolism. Examples of such regulatory pathways are the Ras pathway, the pathway that regulates the breakdown of polyphosphoinositides through phospholipase C, and PI-3-kinase activated pathways, such as the rapamycin-sensitive protein kinase B (PKB/Akt) pathway.

The peptides of the invention have been specifically shown to interfere with the interaction of the PTB domain of Shc and phosphotyrosine-containing peptides based on the sequence around Tyr 490 in activated nerve growth factor receptor and based on the Shc binding site in polyoma middle T antigen. Accordingly, the activity of a peptide of the invention may be confirmed by assaying for the ability of the peptide to interfere with the interaction of the PTB domain of Shc and phosphotyrosine-containing peptides based on the sequence around Tyr 490 in activated nerve growth factor receptor, or based on the Shc binding site in polyoma middle T antigen.

Computer modelling techniques known in the art may also be used to observe the interaction of a peptide of the invention, and truncations and analogs thereof with a PTB domain containing protein (for example, Homology Insight II and Discovery available from BioSym/Molecular Simulations, San Diego, Calif., U.S.A.). If computer modelling indicates a strong interaction, the peptide can be synthesized and tested for its ability to interfere with the binding of the PTB domain of Shc and phosphotyrosine-containing peptides as discussed above.

The peptides of the invention mediate the interactions of PTB domain containing proteins with PTB domain binding sites on proteins such as growth factors and cytokine receptors which regulate pathways that control gene expression, cell division, cytoskeletal architecture and cell metabolism. The peptides may therefore be used in the treatment of conditions involving perturbation of such regulatory pathways. In particular, the peptides may be useful in treating disorders involving excessive proliferation including various forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, head and neck cancers, and nervous system cancers, ovarian cancer, breast cancer, glioblastoma, benign lesions such as papillomas, arthrosclerosis, angiogenesis, and viral infections, in particular HIV infections; and autoimmune diseases including systemic lupus erythematosus, Wegener's granulomatosis, rheumatoid arthritis, sarcoidosis, polyarthritis, pemphigus, pemphigoid, erythema multiforme, Sjogren's syndrome, inflammatory bowel disease, multiple sclerosis, myasthenia gravis, keratitis, scleritis, Type I diabetes, insulin-dependent diabetes mellitus, Lupus Nephritis, and allergic encephalomyelitis.

The invention also relates to a pharmaceutical composition comprising a peptide of the invention for use as an antagonist of the interaction of a PTB domain containing protein, preferably Shc and a PTB domain binding site, preferably an activated growth factor or cytokine receptor.

The peptides of the invention may be formulated into pharmaceutical compositions for adminstration to subjects in a therapeutically active amount and in a biologically compatible form suitable for administration in vivo i.e. a form of the peptides to be administered in which any toxic effects are outweighed by the therapeutic effects.

The peptides may be administered to living organisms including humans, and animals. A therapeutically active amount of the pharmaceutical compositions of the invention is defined as an amount effective, at dosages and for periods of time necessary to achieve the desired result. For example, a therapeutically active amount of a peptide may vary according to factors such as the disease state, age, sex, and weight of the individual. Dosage regime may be adjusted to provide the optimum therapeutic response.

The peptides may be administered in a convenient manner such as by injection (subcutaneous, intravenous, etc.), oral administration, inhalation, transdermal application, or rectal administration. Depending on the route of administration, the peptides may be coated in a material to protect them from the action of enzymes. The peptides may also be used in combination with organic substances for prolongation of their pharmacologic actions. Examples of such organic substances are non-antigenic gelatin, carboxymethylcellulose, sulfonate or phosphate ester of alginic acid, dextran, polyethylene glycol and other glycols, phytic acid, polyglutarnic acid, and protamine.

The compositions described herein can be prepared by per se known methods for the preparation of pharmaceutically acceptable compositions which can be administered to subjects, such that an effective quantity of a peptide is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the peptides in association with one or more pharmaceutically acceptable vehicles or diluents, and contained in buffered solutions with a suitable pH and iso-osmotic with the physiological fluids. The peptides may also be incorporated in liposomes or similar delivery vehicles.

The utility of the peptides and compositions of the invention may be confirmed in in vitro cell penetration assays. For example, the effects of the peptides upon cellular functions in vivo may be confirmed using electroporation techniques (See Raptis, L., and K. L. Firth, DNA and Cell Biology, 9: 615, 1990 and Raptis, L. H. Et al., BioTechniques 18: 104, 1995).

The utility of the peptides and compositions of the invention may also be confirmed in in vivo animal experimental model systems. For example, therapeutic utility in proliferative disorders may be tested by examining the ability of a substance to suppress the growth of a transplantable tumor. Particular in vivo animal models which may be used include the growth of human tumor cell lines (e.g. glioblastomas) in nude mice; and the development of tumors in mice that carry MMTV-polyomavirus middle T antigen or MMTV-neu transgenes, which result in the development of mammary carcinoma.

The following non-limiting examples are illustrative of the present invention:

EXAMPLES

Example 1

The following materials and methods were utilized in the investigations outlined in the example:

Materials and Methods
Cell lines, anti-sera and fusion proteins

CHO cells expressing Wt insulin receptors (White et al., 1988) were grown in F12 medium containing 25 mM Hepes pH 7.4, and 10% fetal bovine serum. NIH3T3 cells expressing Wt and Phe 490 mutant NGF receptor (Stephens et al., 1994) were grown Dulbecco-Vogt's modified Eagle medium (DMEM) containing 10% calf serum (CS). NIH3T3 cells overexpressing the human EGF receptor (Honegger et al., 1987) were grown in DMEM containing 10% CS and 400 $\mu$g/ml G418. The monoclonal anti-insulin receptor antibody 51 was obtained from Dr. I. Goldfine (Forsayeth et al., 1987; Roth et al., 1982). A polyclonal anti-NGF receptor antiserum was raised against NGF receptor carboxy-terminus (Hempstead et al., 1992), the anti-Shc polyclonal serum was raised against a GST-Shc SH2 domain fusion protein. The anti-P.Tyr monoclonal Antibody 4G10 was obtained from UBI (Lake Placid N.Y.). The GST-Shc PTB fusion protein used in the receptor binding experiments described here is identical to GST-ShcB described in van der Geer et al., 1995. The GST-dShc PTB fusion protein has been described previously (Lai et al., 1995).

Immunoprecipitations and PTB Binding Assays

Cells were grown to confluence and starved 16 hr in medium without serum. CHO cells expressing the insulin receptor were stimulated with 100 nM insulin for 5 min at 37° C. NIH3T3 cells expressing NGF receptors were stimulated with 50 ng/ml NGF for 5 min at 37° C., and NIH3T3 cells expressing the human EGF receptor were stimulated with 100 ng/ml EGF for 5 min at 37° C. Control and growth factor stimulated cells were rinsed twice with cold PBS and lysed in 1 ml 50 mM Hepes pH 7.5, 150 mM NaCl, 10% glycerol, 1% Triton X100, 1.5 mM MgCl$_2$, 1 mM EGTA, 100 mM NaF, 10 mM Sodium Pyrophosphate, 500 $\mu$M Sodium Vanadate, 1 mM PMSF, 10 $\mu$g/ml Aprotinin, and 10 $\mu$g/ml Leupeptin (PLC-lysis buffer) per 10 cm dish. Immunoprecipitations and PTB-binding assays in the absence or presence of 2 or 5 $\mu$M competing phosphopeptide were performed exactly as described previously (van der Geer et al., 1995).

Surface Plasmon Resonance Analysis of Phosphopeptides Interacting with the Shc PTB Domain Peptides were synthesized using 9-fluorenyl methoxycarbonyl (Fmoc) solid phase chemistry with direct incorporation of phosphotyrosine as the N-fluorenylmethoxycarbonyl-O-dimethyl-phosphono-L-tyrosine derivative. Cleavage of the peptide from the resin and deprotection was achieved through an 8 hr incubation at 4° C. in trifluoroacetic acid containing 2 M bromotrimethyl silane and a scavenger mixture composed of thioanisole, m-cresol and 1,2-ethanedithiol (1.0:0.5:0.1% by volume). The product was precipitated with cold t-butyl ethylether and collected by centrifugation. Following desalting of the crude material, pure phosphopeptide was isolated using reverse phase HPLC. The authenticity of the phosphopeptide was confirmed by amino acid analysis and mass spectroscopy.

Surface plasmon resonance analysis was carried out using a Biacore apparatus (Pharmacia Biosensor) as described previously (Puil et al., 1994). The peptide L-S-L-L-S-N-P-T-p.Y-S-V-M-R-S-K (SEQ ID NO:23) was immobilized to a biosensor chip through injection of a 0.5 mM solution of the phosphopeptide, in 50 mM HEPES, pH 7.5 and 2 M NaCl, across the chip surface previously activated following procedures outlined by the manufacturer. Injection of anti-phosphotyrosine antibody was used to confirm that successful immobilization of the peptide was achieved. Solutions (100 $\mu$l) containing 1 $\mu$M GST-Shc PTB domain fusion protein and the indicated concentrations of soluble phosphopeptide in 50 mM Na phosphate, pH 7.5, 150 mM NaCl, 0.1 mM EDTA, and 2 mM DTT, were injected across the surface. The amount of bound GST-Shc PTB domain was estimated from the surface plasmon resonance signal at a fixed time following the end of the injection and the percentage bound, relative to injection of GST-Shc PTB domain alone, calculated. The surface was regenerated using 2 M Guanidinium-HCl.

Expression of Torso-DER in Transgenic Flies

Transgenic flies expressing the activated Torso-DER chimeric protein expressed under the control of the heat shock promoter were obtained and protein expression was induced by growing the flies at 37° C. for 45 min after which they were allowed to recover at room temperature for 2.5 hr. Lysates were made as described before (Lai et al., 1995).

I. Identifying Motifs Recognized by the Shc PTB Domain

Figure 1B:
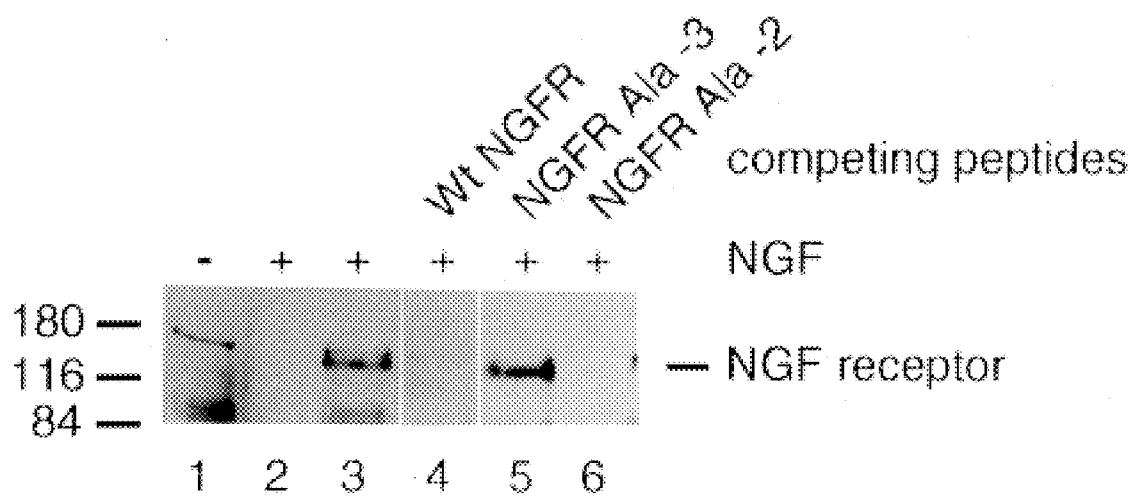
FIG. 1B is the immunoblot shown in FIG. 1A stripped and reprobed with an antiserum raised against the NGF receptor.
Figure 2:
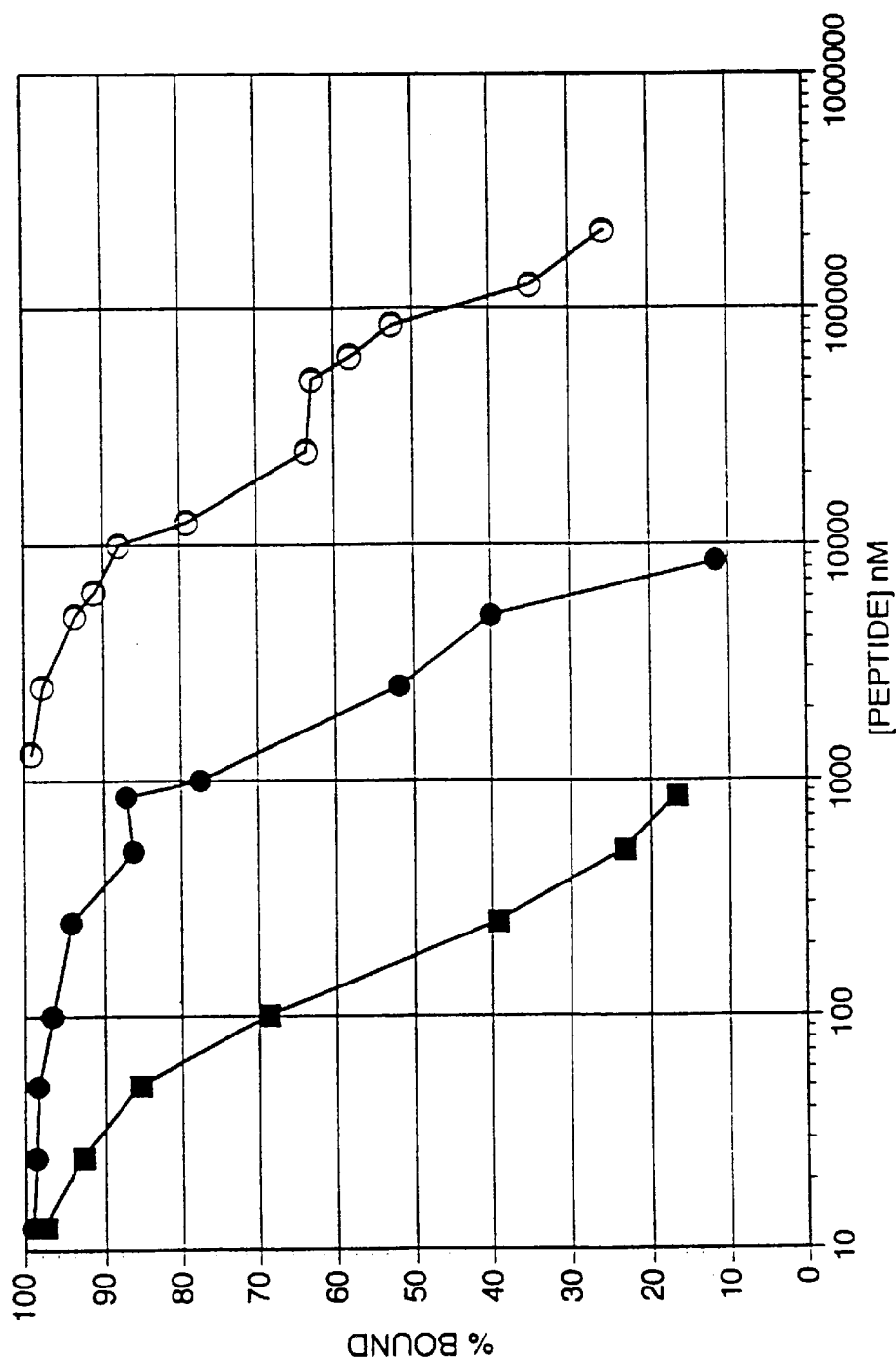
FIG. 2 is a graph showing the results of surface plasmon resonance technology testing the ability of Wt and mutant phosphopeptides, based on the sequence around Tyr 490 the Shc-binding site in the NGF receptor to compete for binding of the GST-Shc PTB domain fusion protein to the immobilized polyoma middle T antigen peptide.

The PTB domain was found to bind tyrosine phosphorylated proteins that contain phosphorylation sites present within the sequence Asn-Pro-X-P.Tyr. To confirm that it is indeed the Asn-Pro-X-P.Tyr motif that is recognized by the PTB domain, it was shown that peptides that contain a phosphotyrosine within the sequence Asn-Pro-X-P.Tyr can compete for binding of the Shc PTB domain to activated growth factor receptors. The specificity was confirmed by sequencing peptides present in a degenerate phosphopeptide library that bind to the Shc PTB domain (Songyang et al., 1995). To investigate the contribution of the Asn and Pro residues within the consensus PTB domain binding site to phosphopeptide recognition, the residues were changed to Ala in a phosphopeptide based on the sequence around Tyr 490, the Shc-binding site in the NGF receptor. Wt and mutant peptides were tested for their ability to compete with NGF receptors, present in lysates of NGF-stimulated cells, for binding to a GST fusion protein containing the Shc PTB domain (FIG. 1A). Bound proteins were detected by anti-P.Tyr immunoblotting. Only the activated NGF receptor bound the Shc PTB domain in vitro. The Wt phosphopeptide (His-Ile-Ile-Glu-Asn-Pro-Gln-P.Tyr-Phe-Ser-Asp, SEQ ID NO:1) competed efficiently for binding. Changing the Asn at position −3 (relative to the P.Tyr) to Ala completely abolished binding, whereas changing the Pro at −2 to Ala reduced the affinity of the PTB-peptide interaction. The identity of the NGF receptor was confirmed by stripping and reprobing the blot with a polyclonal antiserum raised against the NGF receptor (FIG. 1B). To confirm these results and to estimate the contribution of the different residues more precisely, a wide range of concentrations of the different peptides was tested for their ability to inhibit binding of the Shc PTB domain to a phosphotyrosine-containing peptide, based on the sequence around Tyr 250 the Shc-binding site in polyoma middle T antigen, immobilized on a Biacore chip (FIG. 2). The data show that within the Asn-Pro-X-P.Tyr motif the Asn residue is essential for peptide binding by the PTB domain; presence of the Pro residue further increases the affinity approximately ten fold (Table 1). PTB binding depends on phosphorylation of the Tyr residue present within the consensus binding site (Blaikie et al., 1994; Kavanaugh and Williams, 1994; van der Geer et al., 1995). These results are consistent with the presence of Asn-Pro-X-P.Tyr motifs in a variety of receptors for growth factors and cytokines that have been shown to bind Shc.

II. Why the Insulin Receptor Lacks the Ability to bind to Shc

Figure 3:
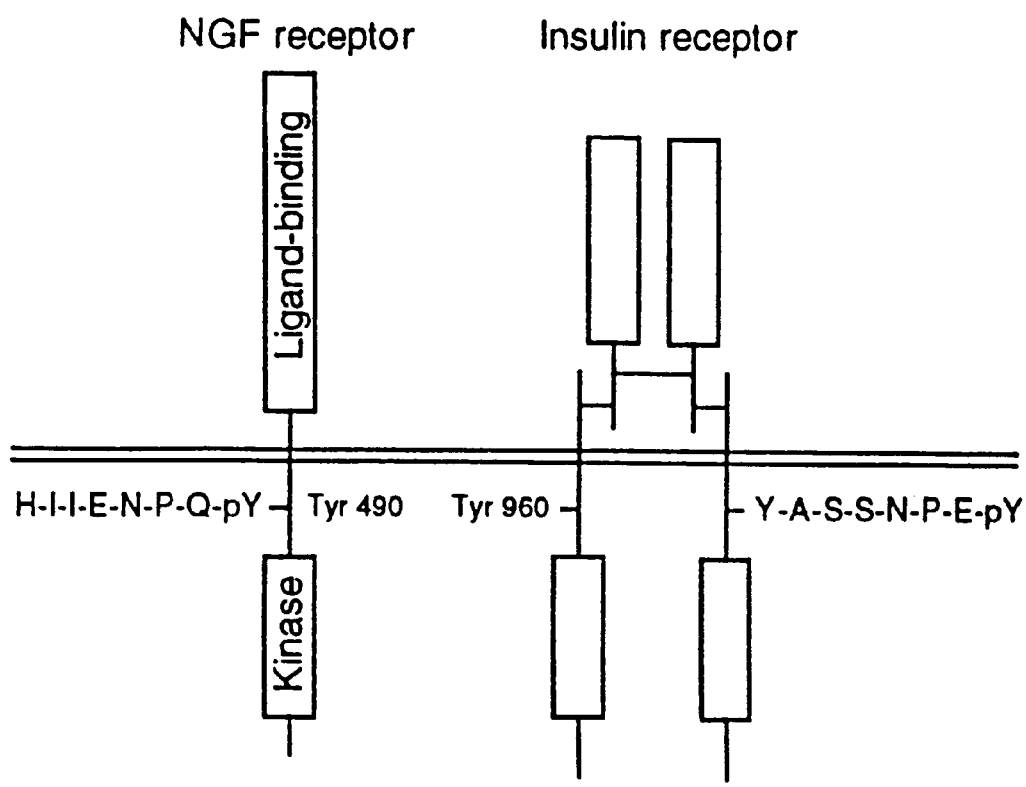
FIG. 3 is a schematic diagram showing the presence of an Asn-Pro-X-P.Tyr motif in the juxta membrane domains of the NGF (SEQ ID NO:56) and insulin receptors (SEQ ID NO:57)
Figure 4A:
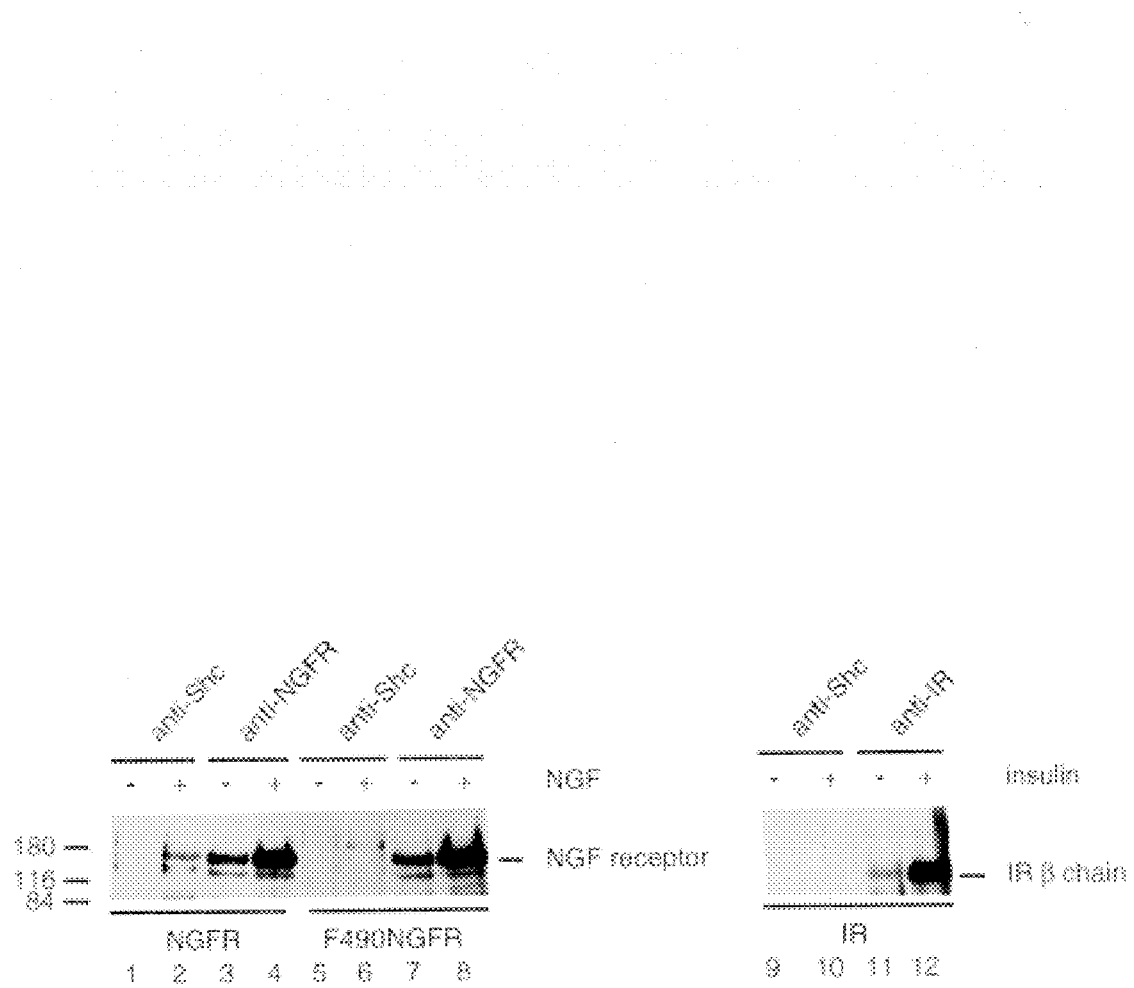
FIG. 4A is an immunoblot showing anti-Shc immunoprecipitates (lanes 1, 2, 5, 6, 9, and 10) from control (lanes 1, 5, and 9) and growth factor-stimulated (lanes 2, 6, and 10) NIH3T3 fibroblasts expressing Wt (lanes 1 and 2; NGFR) or Phe 490 mutant (lanes 5 and 6; F490NGFR) NGF receptors, or CHO cells expressing Wt insulin receptors (lanes 9 and 10; IR) analyzed by anti-P.Tyr immunoblotting; anti-NGF receptor (lanes 3, 4, 7, and 8) and anti-insulin receptor immuno-precipitates (lanes 11 and 12) from control (lanes 3, 7, and 11) and growth factor stimulated (lanes 4, 8, and 12) were analyzed in parallel.
Figure 4B:
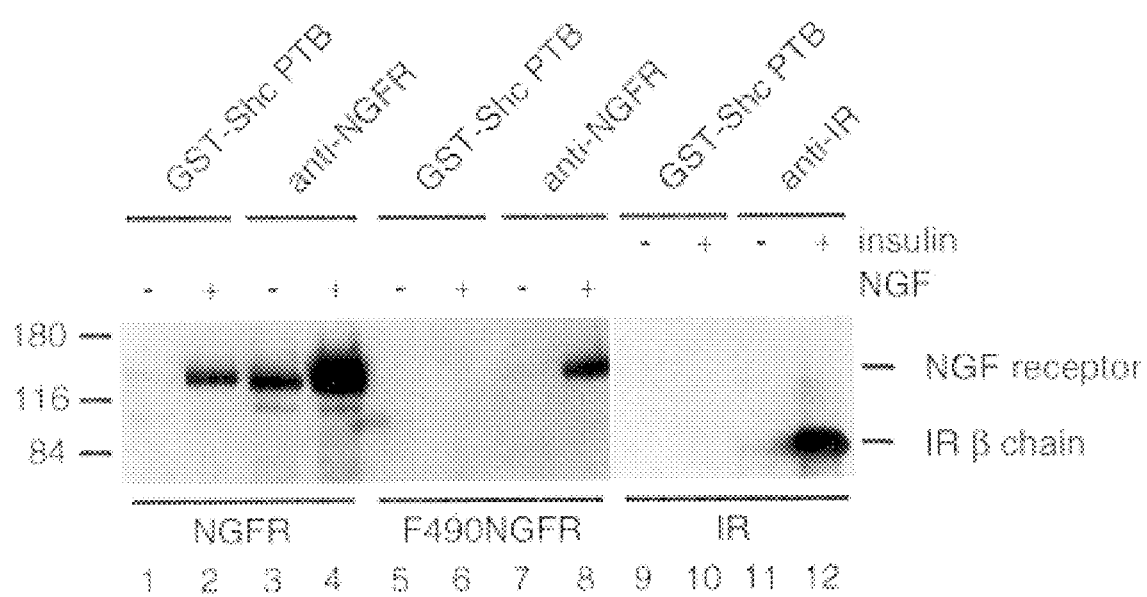
FIG. 4B is an immunoblot showing Wt (lanes 1 and 2) and Phe 490 mutant (5 and 6) NGF receptors present in lysates from control (lanes 1 and 5) and NGF-stimulated (lanes 2 and 6) cells expressing Wt (NGFR) or Phe 490 mutant (F490NGFR) and insulin receptors (IR) present in lysates from control (lane 9) and insulin-stimulated (lane 10) cells incubated with GST-Shc PTB fusion proteins bound to glutathione-agarose, bound proteins were analyzed by anti-P.Tyr blotting.

The insulin receptor, which contains a bona fide autophosphorylation site that is present within the sequence Asn-Pro-Glu-P.Tyr (SEQ ID NO:32), lacks the ability to bind to Shc (Kovacina and Roth, 1993; Pronk et al., 1993). Tyr 960 in the insulin receptor is present in the juxta membrane domain, between the membrane and the kinase domain, in a position very similar to Tyr 490 in the NGF receptor (see FIG. 3). The inability of the insulin receptor to associate stably with Shc was confirmed in coimmunoprecipitation experiments in which Shc immunoprecipitates were analyzed for associated proteins by anti-P.Tyr immunoblotting (FIG. 4A). Wt but not Phe 490 mutant NGF receptors can be detected in Shc immunoprecipitates from NGF-stimulated cells. In contrast, insulin receptors were absent from Shc immunoprecipitates from insulin stimulated CHO cells overexpressing the Wt insulin receptor (CHO-IR cells). To test whether the insulin receptors inability to associate with Shc in cells was reflected in an inability to bind to the Shc PTB domain in vitro, GST fusion proteins containing the Shc PTB domain were incubated with lysates of control and insulin-stimulated CHO-IR cells and bound proteins were visualized by anti-P.Tyr immunoblotting. Wt and Phe 490 NGF receptors were included as controls. The NGF receptor bound to the Shc PTB domain in vitro (FIG. 4B) and binding was dependent on phosphorylation of the NGF receptor at Tyr 490. In contrast, no tyrosine phosphorylated insulin receptors were bound to the Shc PTB domain in vitro (FIG. 4B).

Figure 5A:
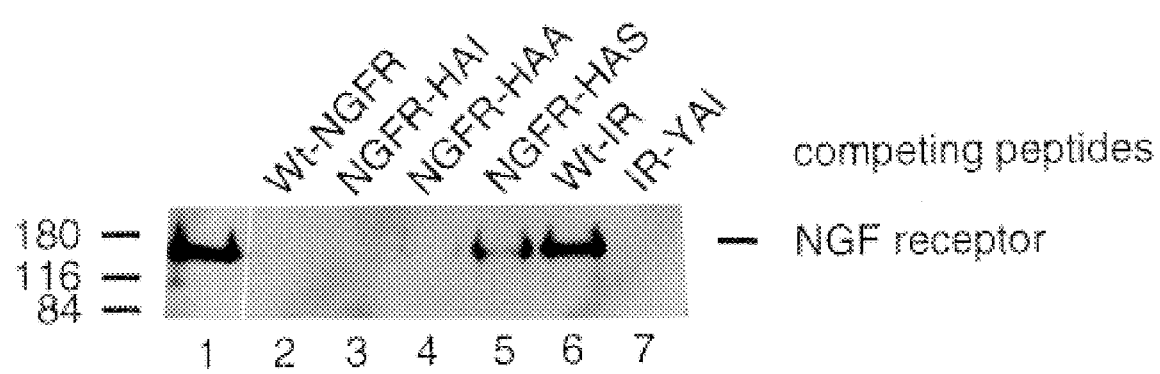
FIG. 5A is an immunoblot showing GST-Shc PTB domain fusion proteins bound to glutathione-agarose after incubation with activated NGF receptors present in lysates of NGF-stimulated cells in the absence (lane 1) or presence (lanes 2–7) of 2 µM competing Wt and mutant phosphotyrosine containing peptides based on the sequence around Tyr 490, the Shc PTB domain binding site in the NGF receptor (lanes 2–5) or Tyr 960 an autophosphorylation site present within an Asn-Pro-X-P.Tyr motif in the insulin receptor (lanes 6 and 7)
Figure 5B:
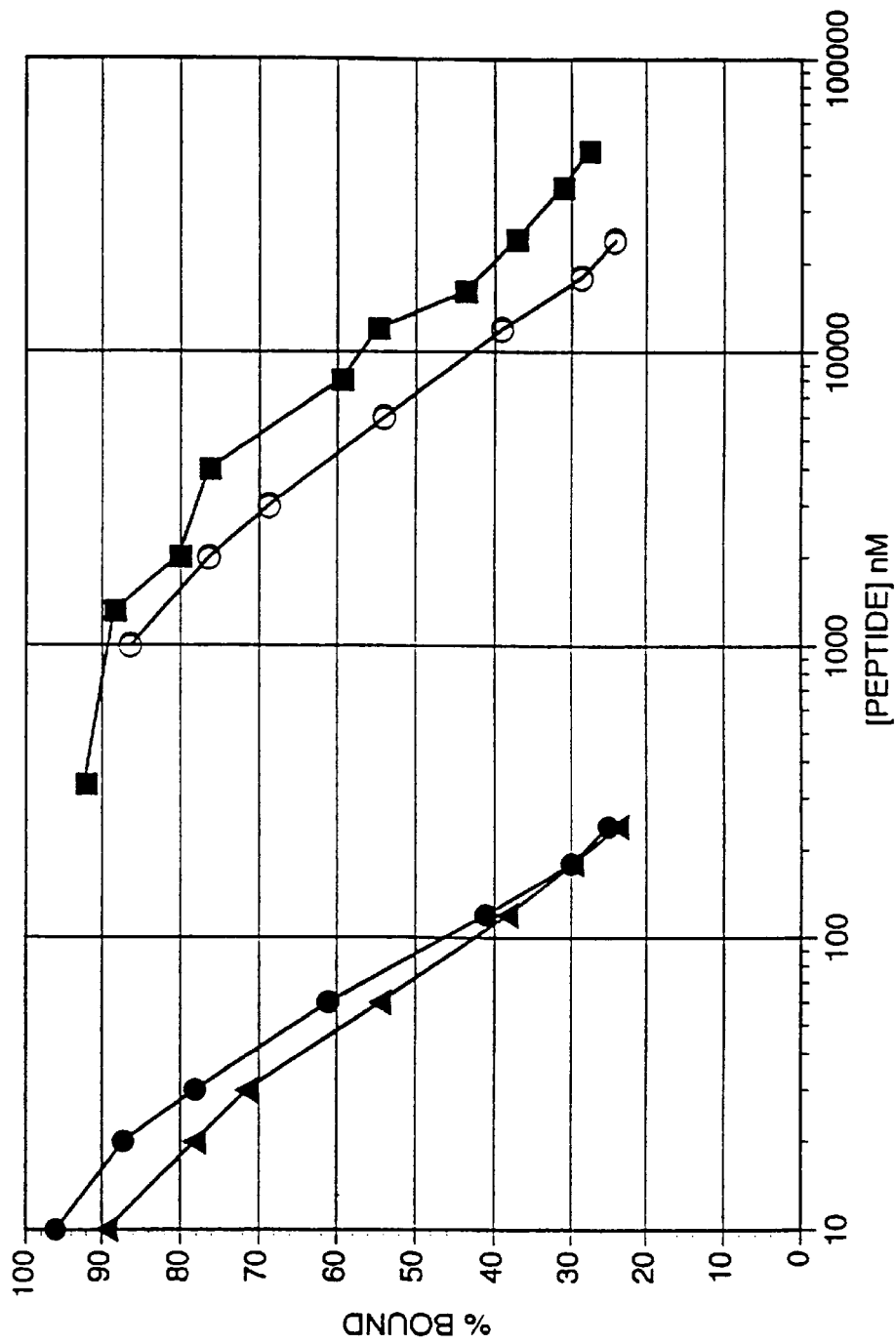
FIG. 5B is a graph showing the results of testing phosphopeptides based on the sequence around Tyr 490, the Shc-binding site in the NGF receptor (H-I-I-E-N-P-Q-p.Y-F-S-D SEQ ID NO:1; (●) or Tyr. 960 in the insulin receptor (Y-A-S-S-N-P-E-p.Y-L-S-A SEQ ID NO:30; (o) and substitutions at position −5 and −6 with respect to the P.Tyr in the NGF receptor peptides (H-A-S-E-N-P-Q-p.Y-F-S-D (SEQ ID NO:31); (■)) and the insulin receptor peptide (Y-A-I-S-N-P-E-p.Y-L-S-A (SEQ ID NO:5); (▲) for their ability to compete for the binding of the GST-Shc PTB domain to the immobilized polyoma middle T antigen peptide (L-S-L-L-S-N-P-T-p.Y-S-V-M-R-S-K) (SEQ ID NO:23)

To investigate the possibility that access to the Asn-Pro-X-P.Tyr motif in the insulin receptor is blocked, the ability of the phosphotyrosine-containing peptide based on the sequence around Tyr 960 in the insulin receptor to compete with the NGF receptor for binding to the Shc PTB domain was tested. In contrast to the NGF receptor phosphopeptide, the insulin receptor peptide was unable to compete (FIG. 5A, lanes 2 and 6, and FIG. 5B). This indicates that the inability of the insulin receptor to bind the PTB domain is retained in this phosphopeptide that starts seven amino acid residues amino-terminal to the P.Tyr (Table 1). The NGF receptor and several other proteins with well defined Shc-binding sites often contain large aliphatic residues at six and five residues amino-terminal of the phosphorylated Tyr residue. These large aliphatic residues are absent from the insulin receptor, which has an Ala and a Ser six and five residues amino-terminal to Tyr 960 (Table 1). To test the possibility that these residues are important for PTB binding, several substitutions at these positions were made in the NGF receptor peptide and mutant peptides were tested for their ability to block binding of the PTB domain to the NGF receptor and to the polyoma middle T antigen phosphopeptide. Changing the Ile six residues upstream of the P.Tyr to an Ala had no effect on the ability to bind to the PTB domain (FIGS. 5A and 5B). In contrast, changing the Ile at −5 to Ala in addition to changing the Ile at −6 reduced the ability to bind to the PTB domain (FIGS. 5A and 5B). Changing the Ile residues at −5 to a Ser in addition to changing the Ile at −6 to Ala, identical to what is found in the insulin receptor, abolished binding (FIGS. 5A and 5B). These data clearly implicate the aliphatic residues five and six residues amino-terminal to the phosphotyrosine in the PTB-binding site as being important for binding to the Shc PTB domain and suggest that changing the Ser, five residues upstream of the P.Tyr in the insulin receptor peptide, to an Ile should increase its ability to bind to the PTB domain dramatically. This was tested and it was found that in contrast to the Wt insulin receptor peptide, which has no measurable affinity for the PTB domain, the mutant insulin receptor peptide competed efficiently with the NGF receptor and the NGF receptor peptide for binding to the PTB domain (FIGS. 5A and 5B). The data presented here (summarized in Table 1) indicate that the Shc PTB domain specifically recognizes P.Tyr residues in the context of a Asn at −3 and a large aliphatic at −5 or −6. A Pro residue at −2 increases the affinity but appears to be non-essential.

III. Characterization of the PTB Domain of Shc

Figure 6A:
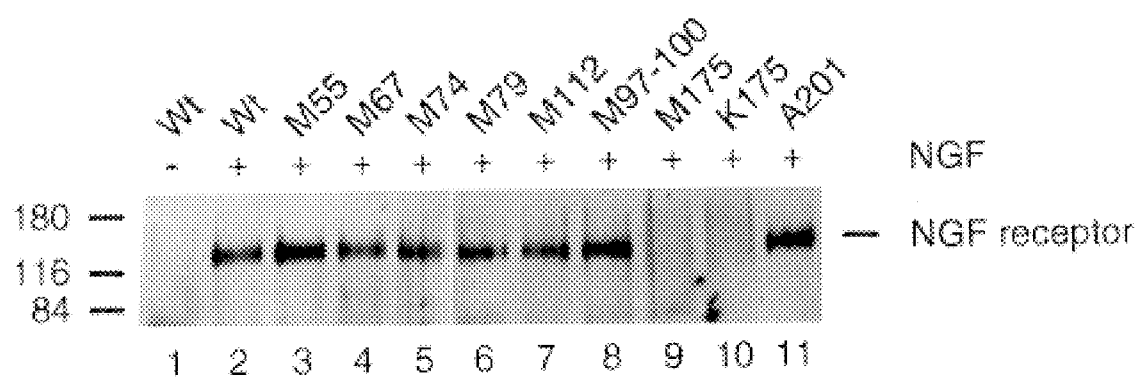
FIG. 6A is an immunoblot showing GST fusion proteins containing Wt (lanes 1 and 2) or mutant (lanes 3–11) Shc PTB domains after incubation with NGF receptors present in lysates of control (lane 1) and NGF-stimulated cells (lanes 2–11), bound proteins were analyzed by anti-P.Tyr blotting.
Figure 6B:
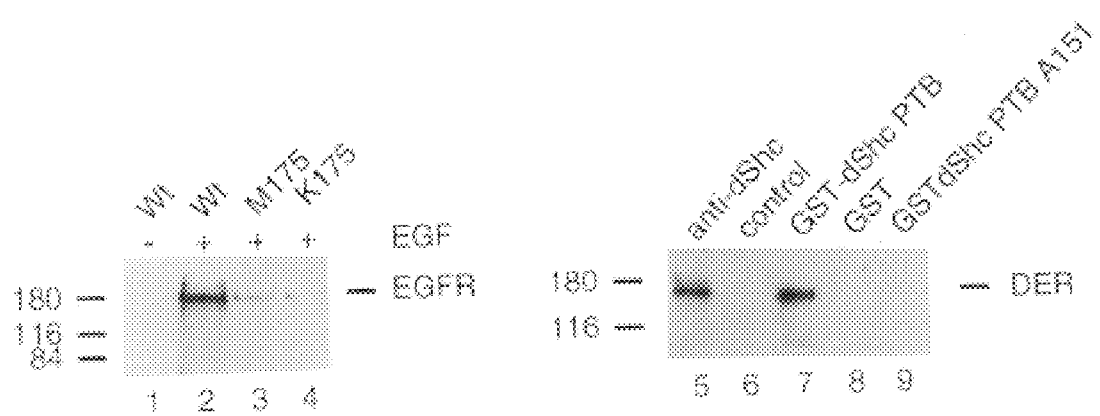
FIG. 6B is an immunoblot showing human EGF receptors bound to GST fusion proteins containing Wt (lanes 1 and 2) or Met 175 (lane 3) and Lys 175 (lane 4) mutant human Shc PTB domains in lysates from control (lane 1) or EGF-stimulated cells (lanes 2–4) analyzed by anti-P.Tyr blotting, and in parallel GST (lane 8) and GST fusion proteins containing Wt (lane 7) or an Ala 151 mutant (lane 9) drosophila Shc PTB domain bound to glutathione-agarose, incubated with fly lysates containing activated Torso-DER chimeric proteins that contain the cytoplasmic domain of DER; bound proteins were detected by anti-P.Tyr blotting.

A comparison of the PTB domains present in Shc and its relatives revealed the presence of a large number of conserved Arg residues. Several conserved Arg are directly involved in P.Tyr binding by SH2 domains. As an initial attempt to characterize PTB domain P.Tyr-binding, all conserved Arg residues in the Shc PTB domain were individually mutated and GST-fusion proteins containing mutant PTB domains were tested for their ability to bind to the activated NGF receptor (FIG. 6A). The three Arg residues and the Lys that are present between residues 97 and 100 were mutated to Met in combination. Of all ten Arg residues tested, only mutation of Arg 175 had a dramatic effect on the affinity of the Shc PTB domain for the activated NGF receptor (FIG. 6A). Both the Met 175 and the Lys 175 mutants were strongly impaired in their binding activity (FIGS. 6A and 6B), indicating that not just a positive charge but a positive charge in the context of an Arg residue is required at this position. The dShc PTB domain contains an Arg at residue 151, which is homologous to Arg 175 in the human Shc. Wt and mutant dShc PTB domains were tested for their ability to bind to the drosophila EGF receptor (DER) (FIG. 6B). The ability of Wt and the 175 mutant human Shc PTB domains to bind to the human EGF receptor were tested in parallel (FIG. 6B). The Wt dShc PTB domain but not the Arg to Ala mutant at position 151 was able to bind efficiently to activated DER in vitro, suggesting that the requirement for the presence of an Arg residue at position 175 in the human Shc PTB domain has been conserved in evolution.

Summary

Shc binding to activated growth factor receptors appears to be an important step in the initiation of signal transduction towards DNA synthesis and cell division or differentiation. Shc binding sites are particularly well characterized in the NGF receptor and in polyoma middle T antigen. In the NGF receptor Shc binds to Tyr 490 in the juxta membrane domain (FIG. 3). Mutation of Tyr 490, in addition to mutation of the PLCγ-binding site, completely blocks NGF-induced neuronal differentiation in PC12 cells (Stephens et al., 1994). Mutation of Tyr 250, which is the Shc binding site, in polyoma middle T antigen blocks cellular transformation (Campbell et al., 1994; Dilworth et al., 1994). The EGF receptor also interacts strongly with Shc, although the precise contribution of different autophosphorylation sites in the EGF receptor carboxy-terminus remains unresolved (Batzer et al., 1994; Okabayashi et al., 1994).

The PTB domain at the amino-terminus of Shc may be the important mediator of Shc-growth factor receptor interactions. Asn-Pro-X-P.Tyr motifs are conserved in a large number of Shc binding proteins and Asn-Pro-X-P.Tyr-containing peptides compete efficiently for Shc PTB binding to activated growth factor receptors, such as the receptors for EGF and NGF (Blaikie et al., 1994; Campbell et al., 1994; Kavanaugh et al., 1995; van der Geer and Pawson, 1995; van der Geer et al., 1995). Using peptide binding studies with mutant peptides, the present inventors characterized the nature of the PTB-binding site. The presence of an Asn residue three residues amino-terminal to the P.Tyr appears to be absolutely essential for binding to the PTB domain. In contrast, the Pro appears to be dispensable for binding to the PTB domain in vitro. Addition of the Pro increases the affinity and this may be important for binding in vivo, consistent with the observation that the Pro appears to be conserved in many Shc PTB-binding sites.

It was found that the activated insulin receptor, which also has an autophosphorylation site contained within an Asn-Pro-X-Tyr motif, does not bind stably to Shc in vivo or in vitro (Kovacina and Roth, 1993; Pronk et al., 1993). Shc, however, becomes phosphorylated in response to insulin and the Shc PTB domain was shown to interact with Tyr 960 in the insulin receptor using the two-hybrid method in yeast (Gustafson et al., 1995). The present inventors have shown that the presence of an aliphatic residue five or six residue amino-terminal to the P.Tyr is important for high affinity binding by the Shc PTB domain. A phosphopeptide with two Ala residues at these positions still binds to the Shc PTB domain but with an affinity that is approximately three fold lower than that for binding of a phosphopeptide with an Ile at either position −6 or −5 (Table 1). The presence of a Ser five residues amino-terminal to the P.Tyr disrupts high affinity binding completely. A peptide, derived from the insulin receptor, that lacked the ability to bind to the Shc PTB domain was changed into a PTB-binding site with a single amino acid substitution at a residue outside the Asn-Pro-X-P.Tyr motif. Conversely, the ability to bind the Shc PTB domain was destroyed by a single amino acid change outside the Asn-Pro-X-P.Tyr motif in an NGF receptor derived phosphopeptide (Table 1). It appears that different PTB domains all recognize Asn-Pro-X-P.Tyr or Asn-X-X-P.Tyr and that further specificity results from interactions of the PTB domain with amino acid residues outside this recognition motif. Furthermore, the presence of particular residues at certain positions within the binding site could prohibit certain PTB domains from binding without affecting the binding of other PTB domains. This is partially illustrated by the observation that the presence of a Ser five residues amino-terminal to the P.Tyr prevents binding of the Shc PTB domain. An understanding of PTB-binding specificity enables accurate predictions to be made as to which proteins will bind to particular PTB-containing adaptor or signalling molecules. In addition, it enables manipulation of the repertoire of PTB domain-containing proteins that are recruited by growth factor receptors without changing the actual phosphate acceptor sites. For instance, phosphorylation of both the insulin receptor substrate 1 (IRS-1) and Shc appears to depend on a low affinity interaction with the insulin receptor at Tyr 960 (Backer et al., 1990; White et al., 1988; Yonezawa et al., 1994). By changing residues amino-terminal of the Asn-Pro-X-P.Tyr motif it may be possible to abolish specifically phosphorylation of either one of these polypeptides by the insulin receptor. Conversely, it may be possible to create an insulin receptor that interacts much stronger with either Shc or IRS-1.

Several Arg residues that are conserved in SH2 domains have been shown to be directly involved in P.Tyr binding (Pawson, 1995; Pawson and Gish, 1992). Based on its functional homology with the SH2 domain further characterization of the PTB domain by mutagenesis of Arg residues that are conserved in the PTB domains of different members of the Shc family has been carried out. The FLVRES sequence (Phe-Leu-Val-Arg-Glu-Ser, SEQ ID NO:33) has been conserved between SH2 domains with the Arg being the only invariant residue present in all SH2 domains described thus far (Pawson, 1995; Pawson and Gish, 1992). An Arg residue present within the sequence YLVRYM (Tyr-Leu-Val-Arg-Tyr-Met, SEQ ID NO:34) (residues 52–57), possibly representing a rudimentary FLVRES (SEQ ID NO:33) motif in the Shc PTB domain, was mutated without an effect on its ligand-binding abilities; mutation of this residue in SH2 domains destroys their ability to bind to phosphotyrosine (Marengere and Pawson, 1992; Mayer et al., 1992). This is consistent with the notion that PTB and SH2 domains are structurally unrelated. The studies described herein have defined an Arg residue in the carboxy-terminus of the PTB domain that is important for its interaction with activated growth factor receptors. This Arg residue is conserved in dShc and its presence was found to be essential for binding of the dShc PTB domain to DER, the drosophila homolog of the EGF receptor. Thus the need for this Arg residue for PTB-ligand interaction has been conserved in evolution between drosophila and man.

As indicated earlier, Shc appears to be important for signal transduction downstream of growth factor and cytokine receptors (Burns et al., 1993; Crowe et al., 1994; Cutler et al., 1993; Lanfrancone et al., 1995; Pelicci et al., 1992; Pronk et al., 1993; Ravichandran et al., 1993; Segatto et al., 1993; Yokote et al., 1994). There is evidence that Shc may be involved in Ras activation presumably through its interaction with Grb2 and Sos (Buday and Downward, 1993; Crowe et al., 1994; Egan et al., 1993; Gale et al., 1993; Li et al., 1993; Myers et al., 1994; Rozakis-Adcock et al., 1993; Rozakis-Adcock et al., 1992; Salcini et al., 1994; Sasaoka et al., 1994).

Example 2

The ability of the peptides listed in Table 2 to inhibit the binding of human Shc PTB domains to activated EGF-receptor (R) or NGF-R (Trk) was investigated. The following materials and methods were used in the assays:

Peptides

The peptides are listed in Table 2. In Table 2 the designation "C" refers to a cyclic peptide; C-1,3,4,5 are cyclized by the amino- and carboxyl termini by an amide bond; C-2 is cyclized by a disulfide bond between two cysteines on each of the N- and C-termini; "P" refers to peptides which have penetrating sequences on the N-terminus where P-1 and P-2 are basic charged penetrating sequences with the latter having phosphorylated tyrosine residues; P-3 and P-4 have a hydrophobic penetrating sequence with the latter having phosphorylated tyrosine residues; and "P-5" was obtained by coupling with penetratin 1 (Appligene) and CGHIIENPQPYFSD (SEQ ID NO:35).

Fusion Proteins

GST-ShcB and GST-R175M fusion proteins were prepared as described in van der Geer et al., 1995.

In vitro binding assay

HER14 cells (3T3 cells expressing EGF-R) were starved in 0.5% CS media for 24 hours and stimulated with 100 ng/ml EGF for 5 min. Cells were lysed and mixed with GST, GST-ShcB or GST-R175M beads. Proteins which bound to beads were resolved on SDS-PAGE and detected by anti-phospho-Tyr antibody (4G10) or by anti-EGF-R.

Results

Inhibition of Binding by Peptides In Vitro

Figure 8:
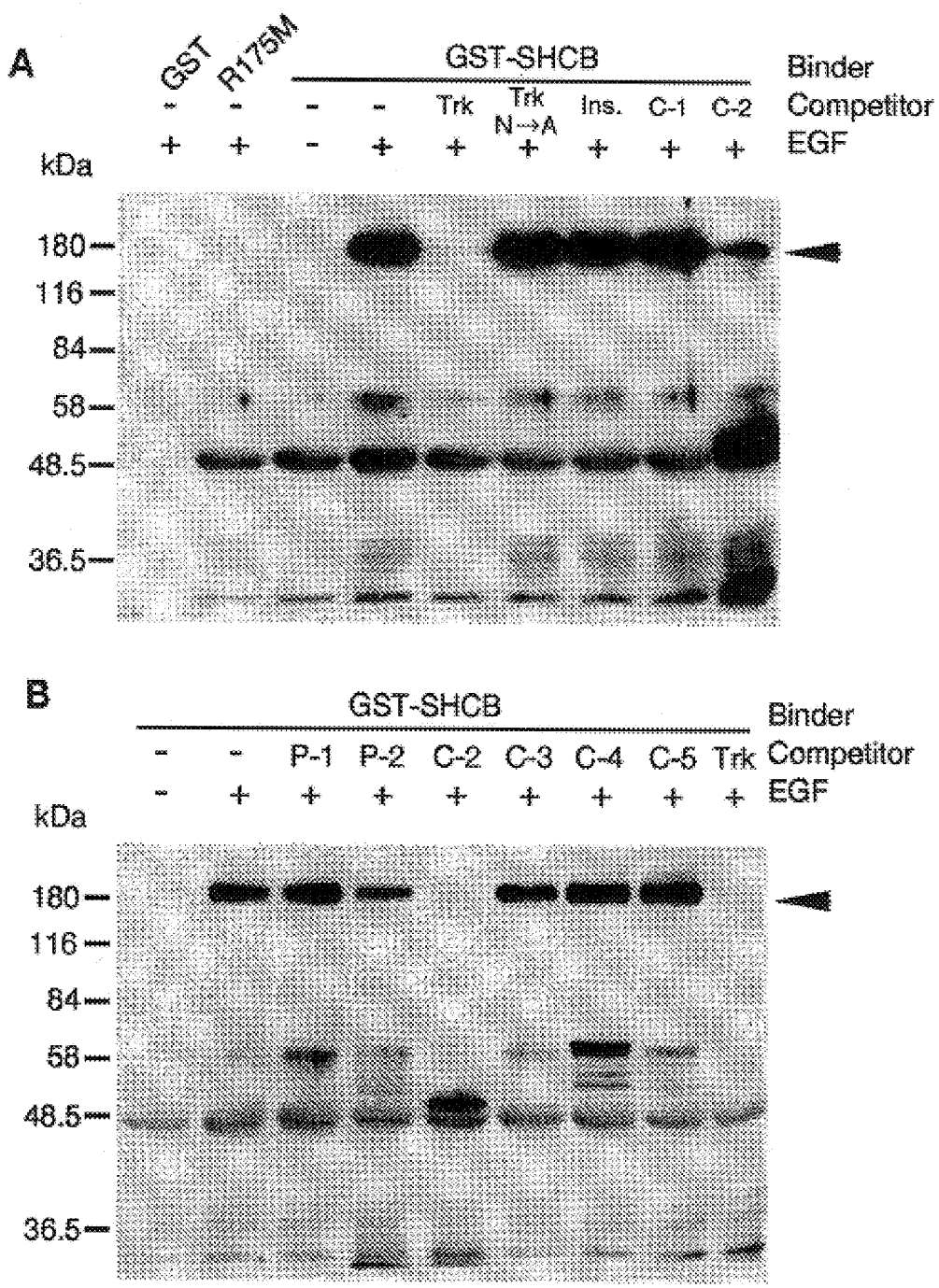
FIG. 8 are immunoblots showing competitive inhibition of EGF receptor binding to GST-ShcB analyzed by anti-phospho-tyrosine antibody.
Figure 9:
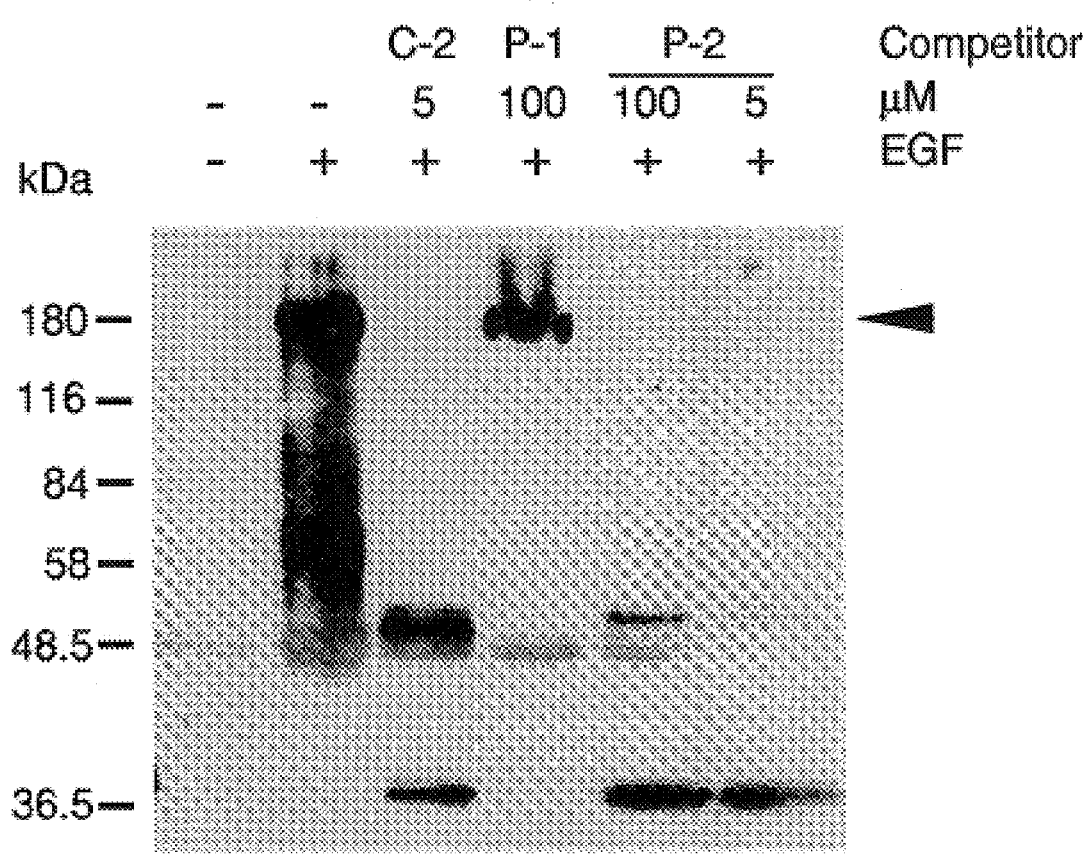
FIG. 9 is an immunoblot showing competitive inhibition of EGF receptor binding to GST-ShcB analyzed by anti-phospho-tyrosine antibody.

The peptides listed in Table 2 were added to cell lysates at 5 $\mu$M, incubated for 30 min., and treated with GST-ShcB beads. Proteins bound to GST-ShcB were detected by anti-phospho-Tyr antibody. A peptide having the Shc PTB binding motif of Trk inhibited the association of Shc and EGF-R while a peptide with an amino acid substitution from Asn to Ala (Trk N to A), or an IRS-1 binding site of insulin receptor (Ins) did not inhibit (FIG. 8, Panel A). The peptide designated C-2 inhibited the binding of Shc and EGF-R completely in vitro (FIG. 8, Panels A, B). P-2, dissolved in Hepes buffer and precipitated, showed weak inhibition (FIG. 8, Panel B). The experiment was repeated with the peptides dissolved in DMSO (FIG. 9). P-2 dissolved in DMSO solution showed strong inhibition at 5 $\mu$M; C-2 inhibited complex formation as described previously; and P-1, which is not phosphorylated on Tyr residues did not inhibit the association of Shc and EGF-R at 100 $\mu$M.

Figure 10:
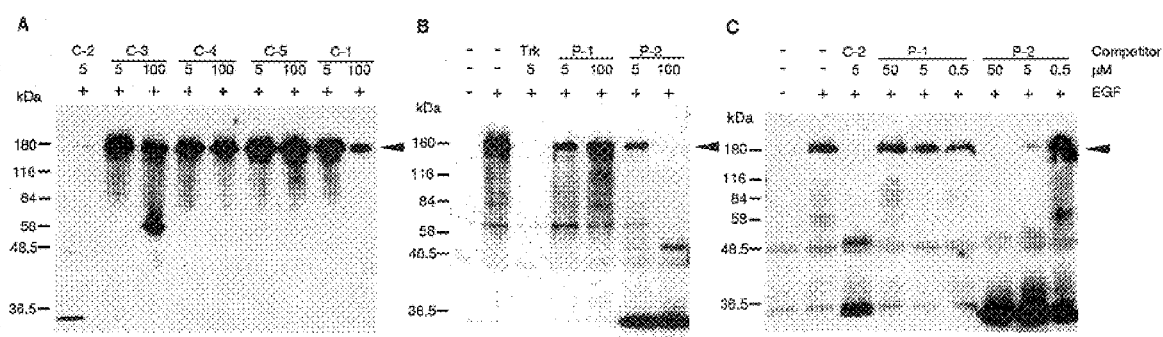
FIG. 10 are immunoblots showing a dose-response analysis in a competitive inhibition assay of EGF receptor binding to GST-ShcB analyzed by anti-phospho-tyrosine antibody.

The dose responses of the peptides was investigated using the in vitro binding assay. While C-2 showed strong inhibition at 5 $\mu$M, C-3, C-4, and C-5, did not inhibit (FIG. 10, Panel A). C-1 exhibited about 50% inhibition at 100 $\mu$M (FIG. 10, Panel A). P-2 (dissolved in Hepes buffer) at a concentration of 100 $\mu$M prevented the association of Shc/EGF-R completely, and it showed slight inhibition at 5 $\mu$M compared to the negative control (P-1) (FIG. 10, Panel B). P-2 dissolved in DMSO showed strong inhibition at 5 $\mu$M while P-2 at 0.5 $\mu$M did not block the protein interaction (FIG. 10, Panel C).

Peptide Localization in Cells

To examine peptide localization, cells were treated with P-1 or P-2 peptide for 4 hours, stained with anti-phospho-Tyr and rhodamine-conjugated antibody, and observed with a confocal microscope. A Z-scan was carried out to make images in each 0.15 $\mu$m section from the top of the cells to the bottom. The image analysis of cell staining demonstrated that the P-2 peptide localized in the cytoplasm of cells, and not in the nucleus. Cells treated with P-1 peptide were not stained by anti-phospho-Tyr antibody, confirming the specifity of the immunofluoroscence staining. In a time course analysis, cells were serum-starved for 24 hours, and incubated with peptide (5 $\mu$M) for various time periods. Cells were stained by anti-phosphoro-Tyr antibody and analyzed under an immunofluoroscence microscope. Cells treated with P-2 peptide retained phospho-peptide for up to 24 hrs. In a dose response experiment, cells were starved in serum-free medium for 24 hours, cultured with peptide at various concentrations, and stained with anti-phospho-tyrosine antibody (4G10) to detect the peptide containing phosphotyrosine residue (red) and by Hoechst 33258 for nuclei (blue). P-2 peptide was detected at 0.5 $\mu$M and 1 $\mu$M in cells . No signals were detected with P-1 peptide in concentraions up to 1 $\mu$M and weak non-specific staining was observed at 5 $\mu$M.

Inhibition of PTB Function in vivo Growth Inhibition of Cells

Figure 11:
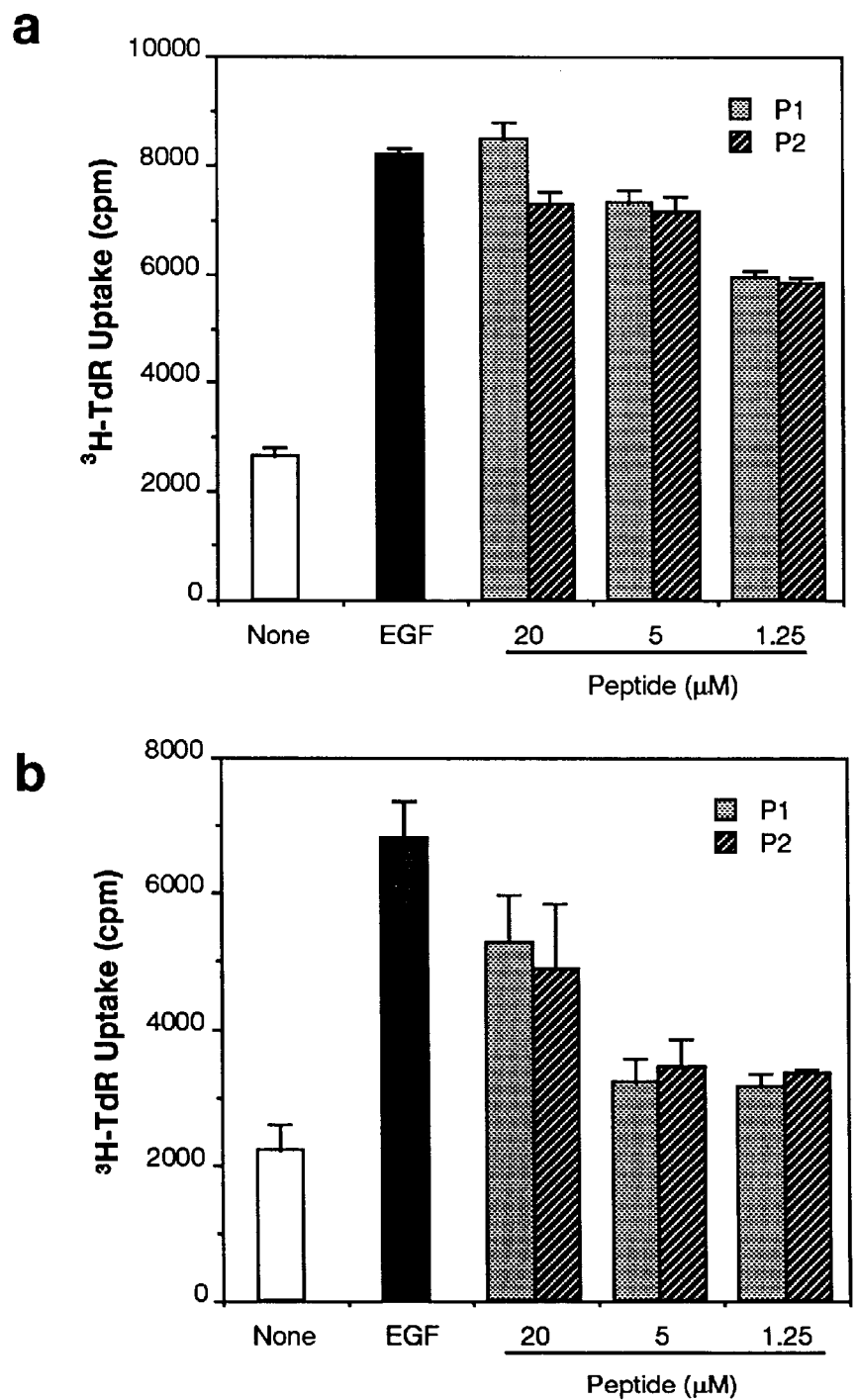
FIG. 11a is a bar graph showing proliferation of HER14 cells treated with peptides of the invention.
FIG. 11b is a bar graph showing proliferication of HER14 cells treated with peptides of the invention.
Figure 12:
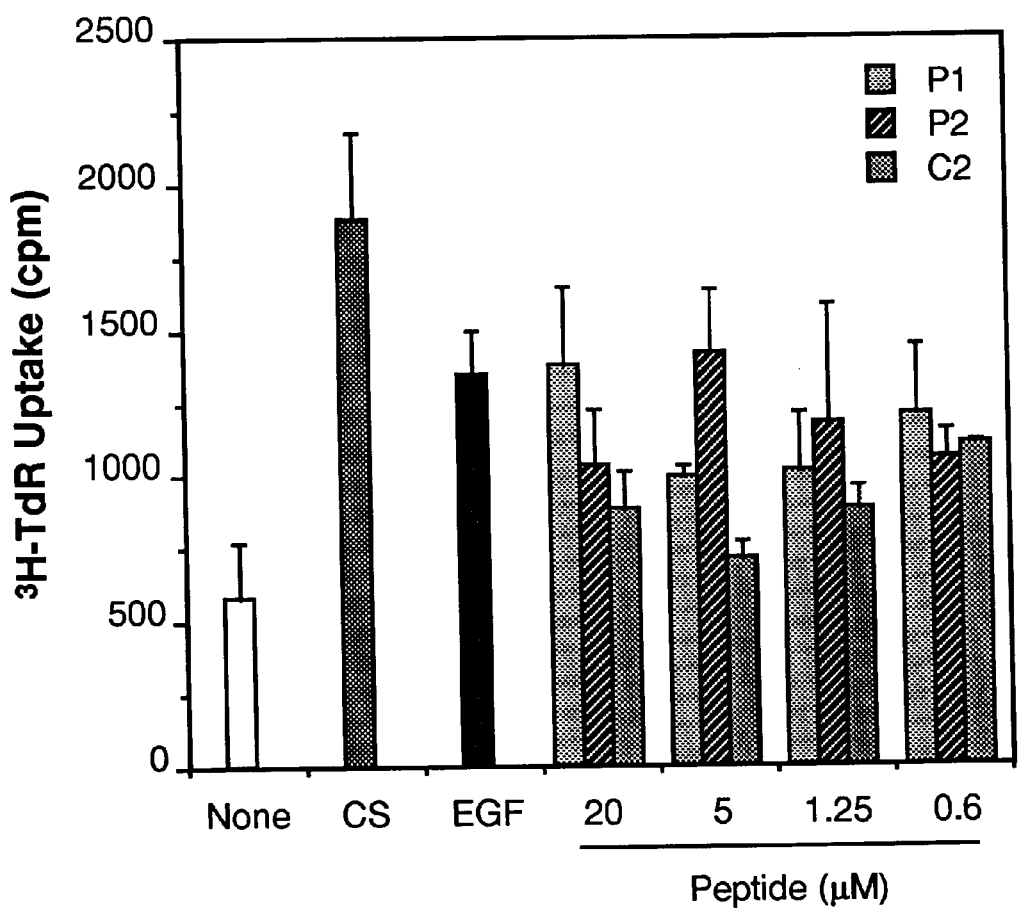
FIG. 12 is a bar graph showing proliferation of HER14 cells treated with peptides of the invention.
Figure 13:
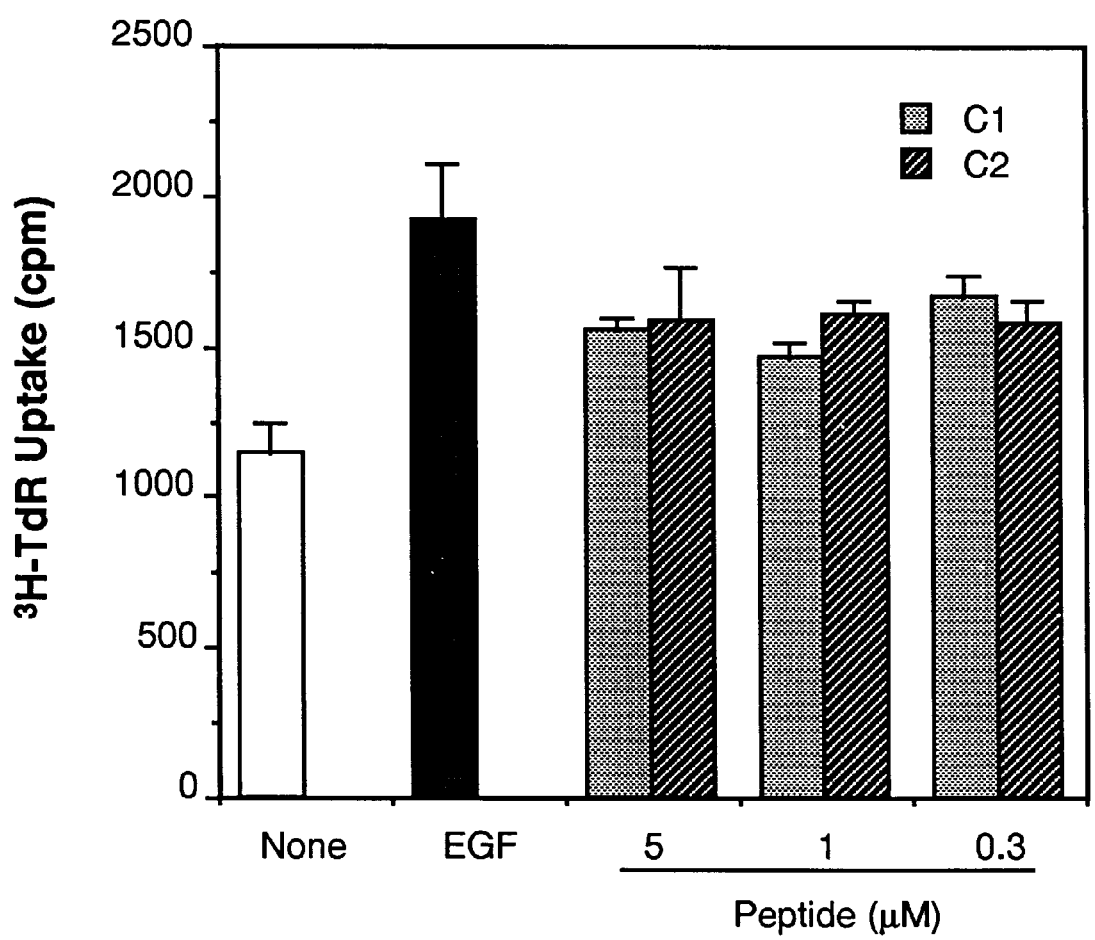
FIG. 13 is a bar graph showing proliferation of HER14 cells treated with cyclic peptides of the invention.

HER14 cells were starved for 24 hours (FIG. 11, Panel a), or 48 hours (FIG. 11, Panel b), treated with P-1 or P-2 peptide for 2 hrs and stimulated with 100 ng/ml EGF. Cell proliferation was measured by $^3$H-TdR uptake (FIG. 11). When cells were starved for 24 hrs, P-1 and P-2 peptides slightly inhibited the proliferation of cells compared to the positive control i.e. EGF alone (a). In cells starved for 48 hrs, both peptides markedly prevented cell proliferation. In particular, about 84% inhibition was observed at 1.25 $\mu$M. Both the P-1 and P-2 peptide demonstrated inhibitory activity, suggesting a non-specific effect was induced by adding peptides. The effect may be due to the internal phosphorylation of P-1 peptide by activated kinase(s) after growth factor stimulation. The above experiments were repeated with cells which were serum starved for 24 hrs. Cells pretreated with P-1 or P-2 did not show any decrease of cell growth rate when compared to EGF treated cells. Cells pretreated with C-2 inhibited cell growth roughly in a dose dependent manner (FIG. 12). The experiment was repeated using C-1 peptide as a negative control, and C-2 did not inhibit cell growth (FIG. 13).

A non-Hodgkin's lymphoma cell line, SupM2 was used in cell proliferation assays as described above. SupM2 has a chromosomal translocation, resulting in the expression of a fusion protein of Alk and Npm. The Alk/Npm fusion protein has a motif which is expected to be a Shc PTB binding domain, and the cell proliferation of SupM2 is believed to be dependent on the Shc pathway. SupM2 cells in the indicated cell number (FIG. 14, Panel a) or at a concentration of 2×10$^4$/well (FIG. 14, Panel b), were grown in serum-free RPMI 1640 medium for 24 hr, treated with peptide for 2 hrs, then, stimulated with 20% FBS overnight, and monitored by $^3$H-tdR pulse. P-1 and P-2 peptides inhibited cell growth to background level (FIG. 14), and cell proliferation was completely inhibited at 70 nM. To examine the optimum dose of peptides, serial dilutions of peptides were used in the assay. At 60 pM, both peptides suppressed the cell growth completely.

Inhibition of PTB Function in vivo. MAPK Activation

Figure 15:
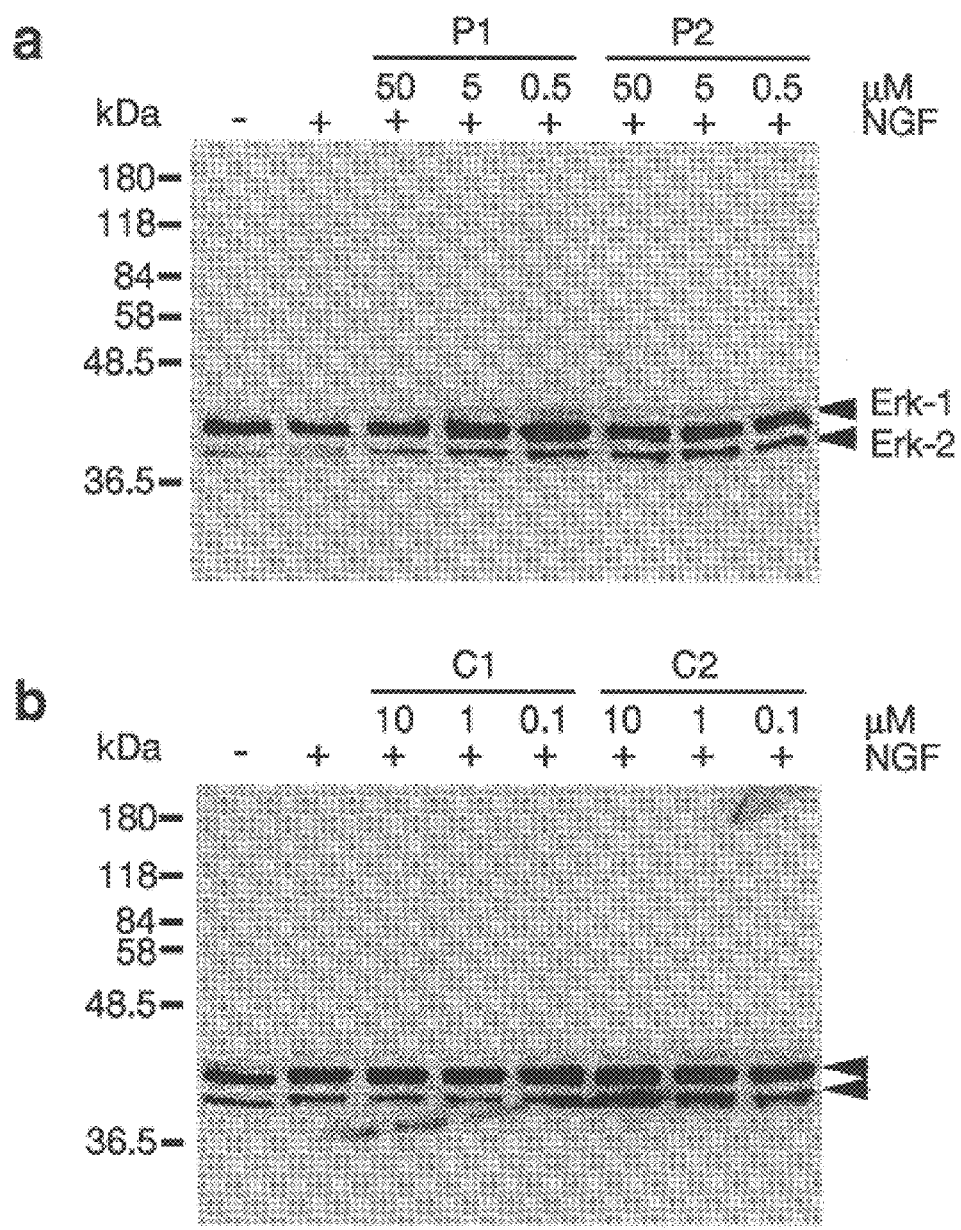
FIG. 15a is an immunoblot showing MAPK activation on PC12 cells treated with peptides of the invention.
FIG. 15b is an immunoblot showing MAPK activation on PC12 cells treated with peptides of the invention.

The phosphorylation state of MAPK was examined after treatment with the peptides. PC12 cells were treated with peptide, stimulated with 50 ng/ml NGF, and a cell lysate was prepared. Proteins were resolved on acrylamide gel to separate phosphorylated- and non-phosphorylated MAPK. Erk-1 was detected by Western blotting. FIG. 15, Panel a shows the series of samples treated with P-1 or P-2, and Panel b shows the samples treated with C-1 or C-2. When cells were treated with NGF, the bands expected for Erk-1 and Erk-2 were slightly shifted and showed higher molecular weights, demonstrating phosphorylation of Erk-1 and Erk-2. However, no inhibition was detected in the group treated with P-2 or C-2. To confirm this result, cell lysates of PC12 described above were immunoprecipitated with anti-Erk-1 antibody, and the proteins were detected by anti-phospho-Tyr antibody (FIG. 16). In FIG. 16, Panel a shows samples treated with P-1 or P-2, and Panel b shows samples treated with C-1 or C-2. Two major bands were detected with predicted molecular weights of about 47 kDa and about 42 kDa, respectively. A weak band of 47 kDa was detected in a sample treated with preimmune serum. Therefore, pp47 appeared to be a non-specific protein whereas pp42 is phosphorylated Erk-1. No differences in phosphorylation state of Erk-1 were observed among the groups treated with the peptides.

The above described experiment was repeated using 3T3Trk cells stimulated with NGF. The results were similar to that obtained with PC12 cells. No specific inhibition of Erk-1 and Erk-2 phosphorylation by C-2 or P-2 was observed.

In summary, the efficacy of the peptides in Table 2 were assayed for the ability to inhibit the interaction between the Shc PTB domain and growth factor receptors. P-2 and C-2 peptides demonstrated strong inhibitory activities in in vitro binding assays. P-2 was found to localize in the cell cytoplasm by simply adding the peptide into the culture medium. In preliminary experiments, specific inhibition of cell growth or of MAPK activation by the peptides was not demonstrated in vivo. However, the in vivo assay system requires further optimization.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

Below full citations are set out for the references referred to in the specification is a listing and detailed legends for the figures are provided.

The application contains sequence listings which form part of the application.

Full Citations for References Referred to in the Specification

J. M. Backer, C. R. Kahn, D. A. Cahill, A. Ullrich and M. F. White (1990) *J Biol. Chem.*, 265, 16450–16454.

A. G. Batzer, D. Rotin, J. M. Urena, E. Y. Skolnik and J. Schlessinger (1994) *Mol. Cell. Biol.*, 14, 5192–5201.

P. Blaikie, D. Immanuel, J. Wu, N. Li, V. Yainik and B. Margolis (1994) *J Biol. Chem.*, 269, 32031–32034.

L. Buday and J. Downward (1993) *Cell*, 73, 611–620.

L. A. Burns, L. M. Karnitz, S. L. Sutor and R T. Abraham (1993) *J Biol. Chem.*, 268, 17659–17661.

K. S. Campbell, E. Ogris, B. Burke, W. Su, K. R. Auger, B. J. Druker, B. S. Schaffhausen, T. M. Roberts and D. C. Pallas (1994) *Proc. Nat. Acad. Sci. USA*, 91, 6344–6348.

A. J. Crowe, J. McGlade, T. Pawson and M. J. Hayman (1994) *Oncogene*, 9, 537–544.

R. L. Cutler, L. Liu, J. E. Damen and G. Krystal (1993) *J Biol. Chem.*, 268, 21463–21465.

S. M. Dilworth, C. E. Brewster, M. D. Jones, L. Lanfrancone, G. Pelicci and P. G. Pelicci (1994) *Nature*, 367, 87–90.

S. E. Egan, B. W. Giddings, M. W. Brooks, L. Buday, A. M. Sizeland and R. A. Weinberg (1993) *Nature*, 363, 45–51.

J. R. Forsayeth, A. Montemurro, B. A. Maddux, R. DePirro and I. D. Goldfine (1987) *J. Biol. Chem.*, 262, 4134–4140.

N. W. Gale, S. Kaplan, E. J. Lowenstein, J. Schlessinger and D. Bar-Sagi (1993) *Nature*, 363, 88–92.

T. A. Gustafson, W. He, A. Craparo, C. D. Schaub and T. J. O'Neill (1995) *Mol. Cell. Biol.*, 15, 2500–2508.

B. L. Hempstead, S. J. Rabin, L. Kaplan, S. Reid, L. Parada and D. R. Kaplan (1992) *Neuron*, 9, 883–896.

A. M. Honegger, T. J. Dull, S. Felder, E. Van Obberghen, F. Bellot, D. Szapary, A. Schmidt, A. Ullrich and J. Schlessinger (1987) *Cell*, 51, 199–209.

W. M. Kavanaugh, C. W. Turck and L. T. Williams (1995) *Science*, 268, 1177–1179.

W. M. Kavanaugh and L. T. Williams (1994) *Science*, 266, 1862–1865.

K. S. Kovacina and R. A. Roth (1993) *Biochem. Biophys. Res. Commun.*, 192, 1303–1311.

K. -M. V. Lai, J. P. Olivier, G. D. Gish, M. Henkemeyer, J. McGlade and T. Pawson (1995) *Mol. Cell. Biol.*, 15: 4810–4818.

L. Lanfrancone, G. Pelicci, M. F. Brizzi, M. G. Arouica, C. Casciari, S. Giuli, L. Pegararo, T. Pawson and P. G. Pelicci (1995) *Oncogene*, 10, 905–917.

N. Li, A. Batzer, R. Daly, V. Yajnik, E. Skolnik, P. Chardin, D. Bar-Sagi, B. Margolis and J. Schiessinger (1993) *Nature*, 363, 85–88.

L. E. M. Marengere and T. Pawson (1992) *J. Biol. Chem.*, 267, 22779–22786.

B. J. Mayer, P. K. Jackson, R. A. Van Etten and D. Baltimore (1992) *Mol. Cell. Biol.*, 12, 609–618.

M. J. Myers, L. M. Wang, X. J. Sun, Y. Zhang, L. Yenush, J. Schlessinger, J. H. Pierce and M. F. White (1994) *Mol. Cell. Biol.*, 14, 3577–3587.

A. Obermeier, R. A. Bradshaw, K. Seedorf, A. Choidas, J. Schlessinger and A. Ullrich (1994) *EMBO J.*, 13, 1585–1590.

Y. Okabayashi, Y. Kido, T. Okutani, Y. Sugimoto, K. Sakaguchi and M. Kasuga (1994) *J. Biol. Chem.*, 269, 18674–18678.

T. Pawson (1995) *Nature*, 373, 573–580.

T. Pawson and G. D. Gish (1992) *Cell*, 71, 359–362.

G. Pelicci, L. Lanfrancone, F. Grignani, J. McGlade, F. Cavallo, G. Forni, I. Nicoletti, F. Grignani, T. Pawson and P. G. Pelicci (1992) *Cell,* 70, 93–104.

G. J. Pronk, J. McGlade, G. Pelicci, T. Pawson and J. L. Bos (1993) *J. Biol. Chem.,* 268 5748–5753.

L. Puil, J. Liu, G. D. Gish, G. Mbamalu, D. Bowtell, P. G. Pelicci, R. Arlinghaus and T. Pawson (1994) *EMBO J.,* 13, 764–773.

K. S. Ravichandran, K. K. Lee, Z. Songyang, L. C. Cantley, P. Burn and S. J. Burakoff (1993) *Science,* 262, 902–905.

R. A. Roth, D. J. Cassell, K. Y. Wong, B. A. Maddux and I. D. Goldfine (1982) *Proc. Natl. Acad Sci. USA,* 79, 7312–7316.

M. Rozakis-Adcock, R. Fernley, J. Wade, T. Pawson and D. Bowtell (1993) *Nature,* 363, 83–85.

M. Rozakis-Adcock, J. McGlade, G. Mbamalu, G. Pelicci, R. Daly, S. Thomas, J. Brugge, P. G. Pelicci, J. Schlessinger and T. Pawson (1992) *Nature,* 360, 689–692.

A. E. Salcini, J. McGlade, G. Pelicci, I. Nicoletti, T. Pawson and P. G. Pelicci (1994) *Oncogene,* 9, 2827–2836.

T. Sasaoka, B. Draznin, J. W. Leitner, W. J: Langlois and J. M. Olefsky (1994) *J. Biol. Chem.,* 269, 10734–10738.

O. Segatto, G. Pelicci, S. Giuli, G. Digiesi, F. P. Di, J. McGlade, T. Pawson and P. G. Pelicci (1993) *Oncogene,* 8, 2105–2112.

Z. Songyang, B. Margolis, M. Chaudhuri, S. E. Shoelson and L. C. Cantley (1995) *J Biol. Chem.,* 270, 14863–14866.

Z. Songyang, S. E. Shoelson, J. McGlade, P. Olivier, T. Pawson, X. R. Bustelo, M. Barbacid, H. Sabe, H. Hanafusa, T. Yi, R. Ren, D. Baltimore, S. Ratnofsky, R. A. Feldman and L. C. Cantley (1994) *Mol. Cell. Biol.,* 14, 2777–2785.

R. M. Stephens, D. M. Loeb, T. D. Copeland, T. Pawson, L. A. Greene and D. R. Kaplan (1994) *Neuron,* 12, 691–705.

P. van der Geer and T. Pawson (1995) *TiBS,* 20, 277–280.

P. van der Geer, S. Wiley, V. K.-M. Lai, J. P. Olivier, G. Gish, R. Stephens, D. Kaplan, S. Shoelson and T. Pawson (1995) *Curr. Biol.,* 5, 404–412.

M. F. White, J. N. Livingston, J. M. Backer, V. Lauris, T. J. Dull, A. Ullrich and C. R. Kahn (1988) *Cell,* 54, 641–649.

K. Yokote, S. Mori, K. Hansen, J. McGlade, T. Pawson, C. H. Heldin and W. L. Claesson (1994) *J. Biol. Chem.,* 269, 15337–15343.

K. Yonezawa, A. Ando, Y. Kaburagi, R. Yamamoto-Honda, T. Kitamura, K. Hara, M. Nakafiiku, Y. Okabayashi, T. Kadowaki, Y. Kaziro and M. Kasuga (1994) *J. Biol. Chem.,* 269, 4634–4640.

Damen, J. E. et al., *Proc. Natl. Acad. Sci. U.S.A.* 93(4), 1689–1693, 1996.

Detailed Figure Legends

FIG. 1A and FIG. 1B. The Asn present within the Asn-Pro-X-P.Tyr motif is essential for binding to the PTB domain. FIG. 1A. GST (lane 2) and GST Shc PTB (lanes 1, 3–6) fusion proteins bound to glutathione-agarose were incubated with NGF receptors present in lysates from control (lane 1) and NGF-stimulated (lanes 2–7) cells in the absence (lane 1–3) and presence of Wt (lane 4) and mutant (lanes 5 and 6) competing P.Tyr containing peptides, based on the sequence around Tyr 490 the Shc PTB domain binding site in the NGF receptor. Bound proteins were analyzed by anti-P.Tyr immunoblotting. Competing peptides, Wt NGF receptor (Wt NGFR): His-Ile-Ile-Glu-Asn-Pro-Gln-P.Tyr-Phe-Ser-Asp (SEQ ID NO:1) (lane 4); NGF receptor Asn(-3)Ala (NGFR Ala −3) mutant: His-Ile-Ile-Glu-Ala-Pro-Gln-P.Tyr-Phe-Ser-Asp (SEQ ID NO:37) (lane 5); NGF receptor Pro(−2)Ala (NGFR Pro −2): His-Ile-Ile-Glu-Asn-Ala-Gln-P.Tyr-Phe-Ser-Asp (amino acids 1–11 of SEQ ID NO:38) (lane 6). FIG. 1B. The blot shown under A was stripped and reprobed with an antiserum raised against the NGF receptor.

FIG. 2. Substitution of either the Asn or the Pro in the PTB-binding site affects its ability to bind to the PTB domain. Surface plasmon resonance technology was used to test the ability of Wt and mutant phosphopeptides, based on the sequence around Tyr 490 the Shc-binding site in the NGF receptor for their ability to compete for binding of the Gst-Shc PTB domain protein to the immobilized polyoma middle T antigen peptide (L-S-L-L-S-N-P-T-P.Y-S-V-M-R-S-K, SEQ ID NO:36). Wt. H-I-I-E-N-P-Q-P.Y-F-S-D: (SEQ ID NO:1): (Δ); Ala −3, H-I-I-E-A-P-Q-P.Y-F-S-D (SEQ ID NO:37): (o); Ala −2, H-I-I-E-N-A-Q-P.Y-F-S-DP (SEQ ID NO:38) (●).

FIG. 3. Presence of a Asn-Pro-X-P.Tyr motif in the juxta membrane domains of the NGF and insulin receptors. Both the NGF receptor and the insulin receptor contain an autophosphorylation site within an Asn-Pro-X-P.Tyr motif in the juxta membrane domain, between the membrane and the kinase domain. In both receptors the tyrosine residues within these motif become phosphorylated upon receptor activation, but in contrast to the NGF receptor, the insulin receptor lacks the ability to stably associate with Shc.

FIG. 4A and FIG. 4B. The Shc PTB domain does not stably bind to the Asn-Pro-X-P.Tyr motif in the insulin receptor. FIG. 4A. Anti-Shc immunoprecipitates (lanes 1, 2, 5, 6, 9, and 10) from control (lanes 1, 5, and 9) and growth factor-stimulated (lanes 2, 6, and 10) NIH3T3 fibroblasts expressing Wt (lanes 1 and 2; NGFR) or Phe 490 mutant (lanes 5 and 6; F490NGFR) NGF receptors, or CHO cells expressing Wt insulin receptors (lanes 9 and 10; IR) were analyzed by anti-P.Tyr immunoblotting. Anti-NGF receptor (lanes 3, 4, 7, and 8) and anti-insulin receptor immunoprecipitates (lanes 11 and 12) from control (lanes 3, 7, and 11) and growth factor stimulated (lanes 4, 8, and 12) were analyzed in parallel. FIG. 4B. Wt (lanes 1 and 2) and Phe 490 mutant (5 and 6) NGF receptors present in lysates from control (lanes 1 and 5) and NGF-stimulated (lanes 2 and 6) cells expressing Wt (NGFR) or Phe 490 mutant (F490NGFR) and insulin receptors (IR) present in lysates from control (lane 9) and insulin-stimulated (lane 10) cells were incubated with GST-Shc PTB fusion proteins bound to glutathione-agarose. Bound proteins were analyzed by anti-P.Tyr immunoblotting. Anti-NGF receptor immunoprecipitates (lanes 3, 4, 7, and 8) and anti-insulin receptor immunoprecipitates (lanes 11 and 12) from control (lanes 3, 7, and 11) and growth factor-stimulated (lanes 4, 8, and 12) cells were analyzed in parallel.

FIG. 5A and FIG. 5B. An aliphatic residue five or six amino acids amino-terminal to the P.Tyr is an important determinant for Shc PTB binding. FIG. 5A. GST-Shc PTB domain fusion proteins bound to glutathione-agarose were incubated with activated NGF receptors present in lysates of NGF-stimulated cells in the absence (lane 1) or presence (lanes 2–7) of 2 μM competing Wt and mutant phosphotyrosine containing peptides based on the sequence around Tyr 490, the Shc PTB domain binding site in the NGF receptor (lanes 2–5) or Tyr 960 an autophosphorylation site present within an Asn-Pro-X-P.Tyr motif in the insulin receptor (lanes 6 and 7). Wt NGF receptor peptide (Wt-NGFR, lane 2): H-I-I-E-N-P-Q-p.Y-F-S-D SEQ ID NO:39; Ala-6 NGF receptor peptide (NGFR-HAI): H-A-I-E-N-P-Q-p.Y-F-S-D (SEQ ID NO:2); Ala-6, Ala-5 NGF receptor peptide (NGFR-HAA): H-A-A-E-N-P-Q-p.Y-F-S-D (SEQ ID NO:40); Ala- 6, Ser-5 NGF receptor peptide (NGFR-HAS): H-A-S-E-N-P-Q-p.Y-F-S-D (SEQ ID NO:41); Wt insulin receptor peptide (Wt-IR): Y-A-S-S-N-P-E-p.Y-L-S-A (SEQ ID NO:42); Ile-5 insulin receptor peptide (IR-YAI): Y-A-I-S-N-P-E-p.Y-L-S-A (SEQ ID NO:5). Bound proteins were analyzed by P.Tyr. blotting. FIG. 5B. Phosphopeptides based on the sequence around Tyr 490, the Shc-binding site in the NGF receptor (H-I-I-E-N-P-Q-p.Y-F-S-D, SEQ ID NO:5 (●)) or Tyr 960 in the insulin receptor (Y-A-S-S-N-P-E-p.Y-L-S-A (SEQ ID NO:42) (o)) and substitutions at position –5 and –6 with respect to the P.Tyr in the NGF receptor peptides (H-A-S-E-N-P-Q-p.Y-F-S-D (SEQ ID NO:41) (■)) and the insulin receptor peptide (Y-A-I-S-N-P-E-p.Y-L-S-A SEQ ID NO:5 (▲)) were tested by surface plasmon resonance analysis technology for their ability to compete for the binding of the GST-Shc PTB domain to the immobilized polyoma middle T antigen peptide (L-S-L-L-S-N-P-T-p.Y-S-V-M-R-S-K, SEQ ID NO:36).

FIG. 6A and FIG. 6B. The requirement for an Arg residue at position 175 in the human Shc PTB domain has been conserved in evolution. FIG. 6A. GST fusion proteins containing Wt (lanes 1 and 2) or mutant (lanes 3–11) Shc PTB domains were incubated with NGF receptors present in lysates of control (lane 1) and NGF-stimulated cells (lanes 2–11). Bound proteins were analyzed by anti-P.Tyr blotting. FIG. 6B. Human EGF receptors bound to GST fusion proteins containing Wt (lanes 1 and 2) or Met 175 (lane 3) and Lys 175 (lane 4) mutant human Shc PTB domains in lysates from control (lane 1) or EGF-stimulated cells (lanes 2–4) were analyzed by anti-P.Tyr blotting. In parallel GST (lane 8) and GST fusion proteins containing Wt (lane 7) or an Ala 151 mutant (lane 9) drosophila Shc PTB domain bound to glutathione-agarose, were incubated with fly lysates containing activated Torso-DER chimeric proteins that contain the cytoplasmic domain of DER; bound proteins were detected by anti-P.Tyr blotting. An anti-Shc (lane 5) and a normal rabbit serum immunoprecipitate (lane 6) from the same fly lysates are shown as controls.

FIG. 8. Peptides Competition in In Vitro Binding Assay. Cell Lysates were preincubated with 5 μM of appropriate peptides for 30 min. at 4° C. Then, proteins were precipitated by each binder, resolved on SDA-PAGE. Detection was carried out by anti-phospho-tyrosine antibody. Ins.:IRS-1 binding domain on insulin-R.

FIG. 9. Competition Assay of Penetrating Peptide. Cell lysates were pre-treated with appropriate peptides. Proteins were precipitated by GST-ShcB and detected by anti-phospho-tyrosine antibody. Peptides were prepared in DMSO solution.

FIG. 10. Dose-Response Analysis of Peptides in in vitro Binding Assay. Cell Lysates were prepared and incubated with appropriate peptides in various concentrations. Proteins were precipitated by GST-ShcB and resolved on 10% SDS-PAGE gel. Anti-phospho-tyrosine antibody was used for detection. P-1 and P-2 peptides were dissolved in Hepes buffer (B), and in DMSO solution (C).

FIG. 11. Proliferation of HER14 cells treated with peptides. Cells were starved for 24 (a) or 48 hrs (b) prior to stimulation. Cells were treated with appropriate peptide for 2 hrs, then stimulated with 100 ng/ml EGF overnight. Cell proliferation was monitored by $^3$H-TdR uptake.

FIG. 12. Proliferation of HER14 cells. HER14 cells were cultured in serum-free D-MEM medium in 96-well plates for 24 hrs. Appropriate peptides were added in various concentrations 2 hrs prior to EGF stimulation. Cell proliferation was induced with 100 ng/ml EGF overnight, then monitored by $^3$H-TdR uptake.

FIG. 13. Proliferation of HIER14 cells treated with cyclic peptides. Cells were starved for 48 hrs in serum-free D-MEM medium. Appropriate peptide was added in various concentrations and cultured for 2 hrs prior to EGF stimulation. Cell proliferation was induced with 100 ng/ml EGF overnight and monitored by $^3$H-TdR uptake.

FIG. 14. Proliferation of SupM2 cells treated with peptides. SupM2 cells were starved in serum-free RPMI 1640 medium for 24 hrs in the indicated cell number (a) or $2\times10^4$/well (b). Cells were treated with penetrating peptide in various concentrations for 2 hrs prior to cell stimulation. Cell proliferation was induced with 20% FPS overnight and monitored by $^3$H-TdR pulse.

FIG. 15. MAPK Activation on PC12 Cells Treated with Peptides. PC 12 cells were treated with appropriate peptide at various concentrations. Cells were stimulated with 50 ng/ml NGF for 5 min., then cell lysates were prepared by standard methods. Each lane contains 10 μg protein and MAPK (Erk-1) was detected by anti-Erk-1 polyclonal Ab. Arrows represent activated Erk-1/2 (b).

FIG. 16. Detection of Activated MAPK on PC12 Cells Treated with Peptides. PC12 cells were treated with peptides for 4 hrs prior to stimulation. Cells were stimulated with 50 ng/ml NGF for 5 min. and cell lysates were prepared according to standard methods. 500 μg of cell lysates were immunoprecipitated with anti-Erk-1 polyclonal antibody, and activated Erk-1 proteins were detected by Western blotting of anti-phospho-tyrosine antibody (4G10). Arrow represents activated (phosphorylated) Erk-1 and asterisk shows non-specific band.

TABLE 1

| Phosphotyrosine-containing peptides | IC 50 |
|---|---|
| H-I-I-E-N-P-Q-P.Y-F-S-D | 175 nM |
| H-I-I-E-A-P-Q-P.Y-F-S-D | 80000 nM |
| H-I-I-E-N-A-Q-P.Y-F-S-D | 2500 nM |
| H-A-I-E-N-P-Q-P.Y-F-S-D | 20 nM |
| H-I-A-E-N-P-Q-P.Y-F-S-D | 250 nM |
| H-A-A-E-N-P-Q-P.Y-F-S-D | 475 nM |
| H-A-S-E-N-P-Q-P.Y-F-S-D | 15000 nM |
| Y-A-S-S-N-P-E-P.Y-L-S-A | 7000 nM |
| Y-A-I-S-N-P-E-P.Y-L-S-A | 90 nM |

Table 1. Peptide competition of the GST-Shc FTB domain binding to a polyoma middle T antigen phosphopeptide (L-S-L-L-S-N-P-T-P.Y-S-V-M-R-S-K, SEQ ID NO: 36). Surface plasmon resonance technology was used to evaluate the ability of phosphopeptides derived from sequences around the Tyr 490, the Shc binding site in the NGF receptor (H-I-I-E-N-P-Q-P.Y-F-S-D, SEQ ID NO:1) and Tyr 960 in the insulin receptor (Y-A-S-S-N-P-P.Y-L-S-A, SEQ ID NO: 42) to bind to the Shc PTB domain. Amino acid substitutions were introduced into the peptides (shown in bold). Peptide concentrations that inhibit ending by 50% ($IC_{50}$) are listed. The SEQ ID NOs. for the peptides from the top to the bottom sequence in the Table are ID Nos. 1, 37, amino acids 1–11 of SEQ ID NO: 38, 43, 3, 40, 41, 42, and 44, respectively.

TABLE 2

| Code | Amino acid sequence | |
|---|---|---|
| Trk wild type | HIIENPQpYFSD | 175 nM |
| | IENPQpYFSD | 4 μM |
| C-1 | Cyclo-(IENPQpYFSPG) | |
| C-2 | CIIENPQpYFC<br>└──SS──┘ | |

TABLE 2-continued

| Code | Amino acid sequence |
|---|---|
| C-3 | Cyclo-(NPQpY) |
| C-4 | Cyclo-(NPQpYG) |
| C-5 | Cyclo-(NPQpYGG) |
| P-1 | RQIKIWFQNRRMKWKK-HIIENPQYFSD |
| P-2 | RQIKIWFQNRRMKWKK-HIIENPQpYFSD |
| P-3 | Biotin-ACA-AAVALLPAVLLALLAP-HIIENPQYFSD |

TABLE 2-continued

| Code | Amino acid sequence |
|---|---|
| P-4 | Biotin-ACA-AAVALLPAVLLALLAP-HIIENPQpYFSD |
| P-5 | CGHIIENPQpYFSD<br>|<br>SS-Biotin-Basic penetrating peptide<br>(RQIKIWFQNRRMKWKK?,<br>amino acids 1–16 of SEQ ID NO:51) |

The SEQ ID NOs. for the Trk wild type peptides are ID. Nos. 1 and 45, and the SEQ ID NOs for C-1, C-2, C-3, C-4, C-5, P-1, P-2, P-3, P-4, and P-5 are ID. Nos. 46, 47, 48, 49, 50, 51, 52, 53, 54, 55, respectively.

---

We claim:

1. A peptide of the formula Ia $$X^1\text{-}A^1\text{-}A^2\text{-}X^2\text{-}Asn\text{-}X^3\text{-}X^4\text{-}P.Tyr\text{-}X^5\text{-}X^6\text{-}X^7 \quad \text{Ia}$$

wherein $X^1$ represents Lys, Arg, His, $X^2$ represents Glu, Asn, Tyr, Thr, Ser, $X^3$ represents Pro, Met, Trp, Phe, Ala, Val, Leu, Ile, Gly, Cys, $X^4$ represents Gln, Asp, Asn, Tyr, Thr, Ser, $X^5$ represents Phe, Trp, Pro, Leu, Ala, Val, Ile, Gly, Cys, Met, $X^6$ represents Ser, Thr, Tyr, Asn, Glu, $X^7$ represents Asp, Glu, and one of $A^1$ and $A^2$ represents Ile and the other of $A^1$ and $A^2$ represents Ile or Ala, which interferes with the interaction of a PTB domain containing protein with a PTB domain binding site.

2. A peptide of the formula Ia $$X^1\text{-}A^1\text{-}A^2\text{-}X^2\text{-}Asn\text{-}X^3\text{-}X^4\text{-}P.Tyr\text{-}X^5\text{-}X^6\text{-}X^7 \quad \text{Ia}$$

wherein $X^1$ represents Ser, Thr, Tyr, Asn or Glu, $X^2$ represents Glu, Asn, Tyr, Thr, Ser, $X^3$ represents Pro, Met, Trp, Phe, Ala, Val, Leu, Ile, Gly, Cys, $X^4$ represents Glu, Asp, $X^5$ represents Phe, Trp, Pro, Leu, Ala, Val, Ile, Gly, Cys, Met $X^6$ represents Ser, Thr, Tyr, Asn, Glu, $X^7$ represents Ala, Val, Leu, Ile, Gly, Cys, Phe, Trp, Met, Pro, and one of $A^1$ and $A^2$ represent Ile and the other of $A^1$ and $A^2$ represents Ala, Val, Leu, Ile, Gly, Cys, Phe, Trp, Met or Pro, which interferes with the interaction of a PTB domain containing protein with a PTB domain binding site.

3. A peptide consisting of the sequence His-Ile-Ile-Glu-Asn-Pro-Gln-P.Tyr-Phe-Ser-Asp; His-Ala-Ile-Glu-Asn-Pro-Gln-P.Tyr-Phe-Ser-Asp; His-Ile-Ala-Glu-Asn-Pro-Gln-P.Tyr-Phe-Ser-Asp; Tyr-Ala-Ile-Ser-Asn-Pro-Glu-P.Tyr-Leu-Ser-Ala; Thr-Trp-Ile-Glu-Asn-Lys-Leu-P.Tyr-Gly-Met-Ser-Asp; Thr-Trp-Ile-Glu-Asn-Lys-Leu-P.Tyr-Gly-Thr-Ser-Asp; Leu-Leu-Leu-Ser-Asn-Pro-Ala-P.Tyr.-Arg-Leu-Leu-Leu; Tyr-Ala-Ser-Ser-Asn-Pro-Glu-P.Tyr-Leu-Ser-Ala-Ser; Val-Ser-Val-Asp-Asn-Pro-Glu-P.Tyr-Leu-Leu-Asn-Ala; Ser-Leu-Leu-Ser-Asn-Pro-Thr-P.Tyr-Ser-Val-Met-Arg; Asn-Glu-Met-Ile-Asn-Pro-Asn-P.Tyr-Ile-Gly-Met-Gly; Glu-Met-Phe-Glu-Asn-Pro-Leu-P.Tyr-Gly-Ser-Val-Ser; Ile-Glu-Asn-Pro-Gln-P.Tyr-Phe; Ala-Glu-Asn-Pro-Gln-P.Tyr-Phe; Ile-Ser-Asn-Pro-Glu-P.Tyr-Leu; or Val-Leu-Ala-Asp-Asn-Pro-Ala-P.Tyr-Arg-Ser-Ala (SEQ. ID. NOs. 1 to 3, 5 to 14, 16, 18 and 19 in the Sequence Listing).

4. A peptide consisting of the sequence Ala-Leu-Leu-Leu-Ser-Asn-Pro-Ala-P.Tyr.-Arg-Leu-Leu-Leu-Ala; Gly-Pro-Leu-Tyr-Ala-Ser-Ser-Asn-Pro-Glu-P.Tyr-Leu-Ser-Ala-Ser-Asp-Val-Phe; Pro-Val-Ser-Val-Asp-Asn-Pro-Glu-P.Tyr-Leu-Leu-Asn-Ala-Gln-Lys; Leu-Ser-Leu-Leu-Ser-Asn-Pro-Thr-P.Tyr-Ser-Val-Met-Arg-Ser-Lys; Val-Ser-Ser-Leu-Asn-Glu-Met-Ile-Asn-Pro-Asn-P.Tyr-Ile-Gly-Met-Gly-Pro-Phe; or Leu-Leu-Leu-Thr-Lys-Pro-Glu-Met-Phe-Glu-Asn-Pro-Leu-P.Tyr-Gly-Ser-Val-Ser-Ser-Phe (SEQ. ID. NOs. 20 to 25 in the Sequence Listing).

5. Cyclo-(Ile-Gly-Asn-Pro-Gln-P.Tyr-Phe-Ser-Pro-Gly, cyclo-(Ile-Ile-Glu-Asn-Pro-Gln-P.Tyr-Phe-Ser-Asp-Ala-Pro-Gly), cyclo-(His-Ile-Ile-Glu-Asn-Pro-Gln-P.Tyr-Phe-Ser-Asp-Ala-Pro-Gly) or Cys-Ile-Ile-Glu-Asn-Pro-Gln-P.Tyr-Phe-Cys (SEQ. ID. NOs. 26 to 29.

6. A method of treating a disorder mediated by the interaction of the PTB domain, comprising the step of delivering to a patient a peptide of the formula Ia:

$$X^1\text{-}A^1\text{-}A^2\text{-}X^2\text{-}Asn\text{-}X^3\text{-}X^4\text{-}P.Tyr\text{-}X^5\text{-}X^6\text{-}X^7 \quad \text{Ia}$$

wherein $X^1$ represents Lys, Arg, His, $X^2$ represents Glu, Asn, Tyr, Thr, Ser, $X^3$ represents Pro, Met, Trp, Phe Ala, Val, Leu, Ile, Gly, Cys $X^4$ represents Gln, Asp, Asn, Tyr, Thr, Ser, $X^5$ represents Phe, Trp, Pro, Leu, Ala, Val, Ile, Gly, Cys, Met, $X^6$ represents Ser, Thr, Tyr, Asn, Glu, $X^7$ represents Asp, Glu, and one of $A^1$ and $A^2$ represents Ile and the other of $A^1$ and $A^2$ represents Ile or Ala, which interferes with the interaction of a PTB domain containing protein with a PTB domain binding site.

7. A pharmaceutical composition for inhibiting the interaction of a PTB domain with a phosphotyrosine-containing protein comprising a peptide and a pharmaceutically acceptable carrier, wherein the peptide is of the formula Ia:

$$X^1\text{-}A^1\text{-}A^2\text{-}X^2\text{-}Asn\text{-}X^3\text{-}X^4\text{-}P.Tyr\text{-}X^5\text{-}X^6\text{-}X^7 \quad \text{Ia}$$

wherein $X^1$ represents Lys, Arg, His, $X^2$ represents Glu, Asn, Tyr, Thr, Ser, $X^3$ represents Pro, Met, Trp, Phe, Ala, Val, Leu, Ile, Gly, Cys, $X^4$ represents Gln, Asp, Asn, Tyr, Thr, Ser, $X^5$ represents Phe, Trp, Pro, Leu, Ala, Val, Ile, Gly, Cys, Met, $X^6$ represents Ser, Thr, Tyr, Asn, Glu, $X^7$ represents Asp, Glu, and one of $A^1$ and $A^2$ represents Ile and the other of $A^1$ and $A^2$ represents Ile or Ala, which interferes with the interaction of a PTB domain containing protein with a PTB domain binding site.

8. A peptide of the formula Ia as claimed in claim 1 wherein $X^1$ represents His.

9. A peptide of the formula Ia as claimed in claim 1 wherein $X^2$ represents Glu.

10. A peptide of the formula Ia as claimed in claim 1 wherein $X^3$ represents Pro.

11. A peptide of the formula Ia as claimed in claim 1 wherein $X^4$ represents Gln.

12. A peptide of the formula Ia as claimed in claim 1 wherein $X^5$ represents Phe.

13. A peptide of the formula Ia as claimed in claim 1 wherein $X^6$ represents Ser.

14. A peptide of the formula Ia as claimed in claim 1 wherein $X^7$ represents Asp.

15. A peptide of the formula Ia:

$$X^1\text{-}Ala\text{-}Ile\text{-}X^2\text{-}Asn\text{-}X^3\text{-}X^4\text{-}P.Tyr\text{-}X^5\text{-}X^6\text{-}X^7$$

wherein $X^1$ represents Lys, Arg, His, $X^2$ represents Glu, Asn, Tyr, Thr, Ser, $X^3$ represents Pro, Met, Trp, Phe, Ala, Val, Leu, Ile, Gly, Cys, $X^4$ represents Gln, Asp, Asn, Tyr, Thr, Ser, $X^5$ represents Phe, Trp, Pro, Leu, Ala, Val, Ile, Gly, Cys, Met, $X^6$ represents Ser, Thr, Tyr, Asn, Glu, $X^7$ represents Asp, Glu, which interferes with the interaction of a PTB domain containing protein with a PTB domain binding site.

16. A peptide of the formula Ia as claimed in claim 1 wherein $A^2$ represents Ile.

17. A peptide of the formula Ia as claimed in claim 2 wherein $X^1$ represents Tyr.

18. A peptide of the formula Ia as claimed in claim 2 wherein $X^2$ represents Ser.

19. A peptide of the formula Ia as claimed in claim 2 wherein $X^3$ represents Pro.

20. A peptide of the formula Ia as claimed in claim 2 wherein $X^4$ represents Glu.

21. A peptide of the formula Ia as claimed in claim 2 wherein $X^5$ represents Leu.

22. A peptide of the formula Ia as claimed in claim 2 wherein $X^6$ represents Ser.

23. A peptide of the formula Ia as claimed in claim 2 wherein $X^7$ represents Ala.

24. A method of treating a disorder mediated by the interaction of the PTB domain, comprising the step of delivering to a patient a peptide of the formula Ia as claimed in claim 2.

25. A pharmaceutical composition for inhibiting the interaction of a PTB domain with a phosphotyrosine-containing protein comprising a peptide as claimed in claim 2 and a pharmaceutically acceptable carrier.

26. A peptide of the formula Ile-Glu-Asn-Pro-Gln-P.Tyr-Phe-Ser-Pro-Gly, SEQ ID NO:17.

* * * * *

UNITED STATES PATENT AND TRADEMARK OFFICE
CERTIFICATE OF CORRECTION

PATENT NO. : 6,028,053
DATED : July 24, 2000
INVENTOR(S) : P. Van der Geer et al.

Page 1 of 1

It is certified that error appears in the above-identified patent and that said Letters Patent is hereby corrected as shown below:

Column 2,
Line 55, replace "Gin" with -- Gln --

Column 6,
Line 14, replace "Gin" with -- Gln --
Line 17, replace "Gin" with -- Glu --
Line 27, replace "Gin" with -- Glu --
Line 49, replace "Gin" with -- Glu --

Column 14,
Line 45, replace "N" with -- $N^a$ --

Column 19,
Line 5, replace "defmed" with -- defined --

Column 20,
Line 39, replace "concentraions" with -- concentrations --

Column 26,
Line 1, replace "HIER" with -- HER --
Line 51, replace "N-P-P-Y" with -- N-P-E-P.Y --
Line 53, replace "ending" with -- binding --

Signed and Sealed this

Twenty-first Day of January, 2003

JAMES E. ROGAN
*Director of the United States Patent and Trademark Office*